US011326207B2

(12) United States Patent
Almogy et al.

(10) Patent No.: US 11,326,207 B2
(45) Date of Patent: May 10, 2022

(54) SEQUENCING USING NON-NATURAL NUCLEOTIDES

(71) Applicant: Ultima Genomics, Inc., Newark, CA (US)

(72) Inventors: Gilad Almogy, Palo Alto, CA (US); Linda Lee, Palo Alto, CA (US)

(73) Assignee: ULTIMA GENOMICS, INC., Newark, CA (US)

( * ) Notice: Subject to any disclaimer, the term of this patent is extended or adjusted under 35 U.S.C. 154(b) by 0 days.

(21) Appl. No.: 16/683,841

(22) Filed: Nov. 14, 2019

(65) Prior Publication Data

US 2020/0216889 A1 Jul. 9, 2020

Related U.S. Application Data

(63) Continuation of application No. PCT/US2018/033517, filed on May 18, 2018.

(60) Provisional application No. 62/508,042, filed on May 18, 2017, provisional application No. 62/633,942, filed on Feb. 22, 2018.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
CPC .............................. C12Q 1/6869; C07H 21/04
See application file for complete search history.

(56) References Cited

U.S. PATENT DOCUMENTS

| 5,409,811 | A | 4/1995 | Tabor et al. |
| 5,674,716 | A | 10/1997 | Tabor et al. |
| 9,404,155 | B2 | 8/2016 | Bortner |
| 2005/0181440 | A1 | 8/2005 | Chee et al. |
| 2007/0087362 | A1 | 4/2007 | Church et al. |
| 2008/0293071 | A1 | 11/2008 | Gelfand et al. |
| 2009/0208961 | A1 | 8/2009 | Bjornson et al. |
| 2010/0035253 | A1* | 2/2010 | Gordon .............. C12Q 1/6825 435/6.11 |
| 2010/0261247 | A1 | 10/2010 | Hanzel et al. |
| 2013/0137091 | A1 | 5/2013 | Gordon et al. |
| 2013/0183663 | A1 | 7/2013 | Wegener et al. |
| 2016/0115533 | A1 | 4/2016 | Fabani et al. |

FOREIGN PATENT DOCUMENTS

| WO | WO-2005080605 | A2 | 9/2005 |
| WO | WO-2018213787 | A1 | 11/2018 |

OTHER PUBLICATIONS

Sherrill et al., Nucleic Acid Analysis Using an Expanded Genetic Alphabet to Quench Fluorescence, 2004, J. Am. Chem. Soc., 126, 4550-4556. (Year: 2004).*

Bowers, et al., Virtual Terminator nucleotides for next generation DNA sequencing, Nat Methods, Aug. 2009, 6(8): 593-95.
Braslavsky, et al., Sequence information can be obtained from single DNA molecules, PNAS, Apr. 1, 2003, 100(7): 3960-64.
Guo et al. Four-color DNA sequencing with 3'-O-modified nucleotide reversible terminators and chemically cleavable fluorescent dideoxynucleotides. PNAS USA 105(27):9145-9150 (2008).
Ju et al. Four-Color DNA Sequencing by Synthesis Using Cleavable Fluorescent Nucleotide Reversible Terminators. PNAS USA 103:19635-19640 (2006).
Kartalov, et al., Microuidic device reads up to four consecutive base pairs in DNA sequencing-by-synthesis, Nucleic Acids Research, 2004, 32, (9):2873-79 EPUB May 20, 2004.
Lee, et al., DNA sequencing with dye-labeled terminators and 17 DNA polymerase: effect of dyes and dNTPs on incorporation of dye-terminators and probability analysis of termination fragments, Nucleic Acids Research, 20(10):2471-83.
Livak, et al., Detection of single base differences using biotinylated nucleotides with very long linker arms, Nucleic Acids Research, 1992, 20(18):4831-37.
Marras, et al., Efficiencies of Fluorescence resonance energy transfer and contact-mediated quenching in oligonucleotide probes, Nucleic Acids Research, 2002, 30(21):e122, 8 pages.
PCT/US2018/033517 International Search Report dated Sep. 18, 2018.
Ramsay, et al. CyDNA: Synthesis and Replication of Highly Cy-Dye Substituted DNA by an Evolved Polymerase. J Am Chem Soc. Apr. 14, 2010; 132(14): 5096-5104.Published online Mar. 17, 2010.doi: 10.1021/ja909180c.
Rosenblum, et al., New dye-labeled terminators for improved DNA sequencing patterns, Nucleic Acids Research, 1997, 25(22): 4500-04.
Tabor, et al., A single residue in DNA polymerases of the *Escherichia coli* DNA polymerase I family is critical for distinguishing between deoxy-and dideoxyribonucleotides. Proc. Natl. Acad. Sci. USA, 92:6339-6343, 1995.
Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.
Tasara, et al., Incorporation of reporter molecule-labeled nucleotides by DNA polymerases. II. High-density labeling of natural DNA, Nucleic Acids Research, 2003, 31(10):2636-46.
EP18802971.4 The Extended European Search Report dated Jan. 14, 2021.
Metzker, M. Sequencing technologies—the next generation. Nat Rev Genet. Jan. 2010;11(1):31-46. doi: 10.1038/nrg2626. Epub Dec. 8, 2009.

* cited by examiner

*Primary Examiner* — Narayan K Bhat
(74) *Attorney, Agent, or Firm* — Wilson Sonsini Goodrich & Rosati

(57) ABSTRACT

The present disclosure provides methods and systems for nucleic acid sequencing. Such systems and methods may achieve context-independent incorporation, have reduced context-dependence or have context-dependence that is amenable to calibration and modeling. Such systems and methods may also reduce misincorporation.

32 Claims, 11 Drawing Sheets

Specification includes a Sequence Listing.

| Nucleotide | Observed Products | Yield of Products by CE analysis | Red Fluorescence on Bead in Flow Cytometry |
|---|---|---|---|
| 1. dUTP* | Pr-U* | 42% | 30 |
| 2. dUTP⁰ | Pr-U⁰ | 38% | 0.2 |
| 3. dTTP | Pr-T | 83% | 0.1 |
| 4. 1:1 dUTP*/dUTP⁰ | Pr-U* | 31% | 24 |
| | Pr-U⁰ | 17% | |
| 5. 1:1 dUTP*/dTTP | Pr-U* | 0% | 0.8 |
| | Pr-T | 82% | |

*FIG. 4*

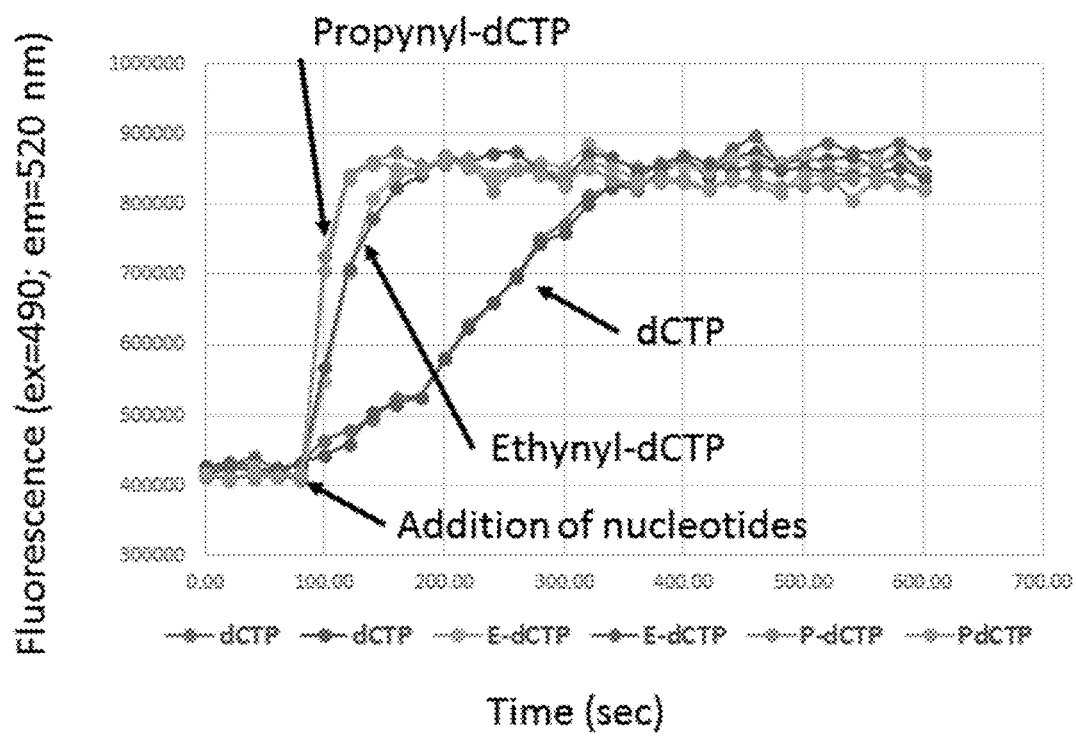
FIG. 7

SEQUENCING USING NON-NATURAL NUCLEOTIDES

CROSS-REFERENCE

This application is a continuation of International Application No. PCT/US18/33517, filed May 18, 2018, which claims the benefit of U.S. Provisional Patent Application No. 62/508,042, filed May 18, 2017, and U.S. Provisional Patent Application No. 62/633,942, filed Feb. 22, 2018, each of which applications is entirely incorporated herein by reference.

SEQUENCE LISTING

The instant application contains a Sequence Listing which has been filed electronically in ASCII format and is hereby incorporated by reference in its entirety. Said ASCII copy, created on Jan. 8, 2020, is named 51024-704_301_Sequence_Listing.txt and is 4.2 kilobytes in size.

BACKGROUND

The goal to elucidate the entire human genome has created interest in technologies for rapid nucleic acid (e.g., DNA) sequencing, both for small and large scale applications. Important parameters are sequencing speed, sequencing accuracy, length of sequences that can be read during a single sequencing run, and the amount of nucleic acid template required to generate sequencing information. Large scale genome projects are currently too expensive and often infeasible to be realistically carried out for a large number of subjects. In particular, sequencing methods that rely on mixtures of labeled and non-labeled nucleotides can result in sequencing errors and issues with reproducible signal production, including such errors and issues associated with variability of incorporation bias of non-labeled nucleotides and context-dependence issues related to incorporation of non-labeled nucleotides at a specific location(s) on a given template nucleic acid molecule.

SUMMARY

As knowledge of the genetic basis for human diseases increases, an ever-increasing need for accurate, high-throughput DNA sequencing that is affordable for clinical applications has been recognized. As such, the present disclosure provides methods and systems for nucleic acid sequencing. Such systems and methods may achieve context-independent incorporation, have reduced context-dependence or have context-dependence that is amenable to calibration and modeling. Such systems and methods may also reduce variability associated with incorporation bias of non-labeled nucleotides and also misincorporation.

In an aspect, the present disclosure provides a method for determining a nucleic acid sequence of a target nucleic acid molecule, comprising: (a) providing a plurality of nucleic acid molecules immobilized to a support, wherein each of said plurality of nucleic acid molecules exhibits sequence homology to said target nucleic acid molecule, and wherein said support is operatively coupled to a detector; (b) directing a nucleotide mixture to said plurality of nucleic acid molecules immobilized to said support, which said nucleotide mixture comprises at least a first subset of nucleotide analogs and a second subset of nucleotide analogs, wherein nucleotide analogs of said first subset and said second subset are different from one another, wherein a given one of said first subset of nucleotide analogs comprises a reporter moiety and is detectable by said detector, and wherein a given one of said second subset of nucleotide analogs is not detectable by said detector; (c) incorporating said nucleotide mixture comprising at least said first subset of nucleotide analogs and said second subset of nucleotide analogs into said plurality of nucleic acid molecules; (d) using said detector to detect said given one of said first subset of nucleotide analogs; and (e) repeating (c) and (d), thereby determining said nucleic acid sequence of said target nucleic acid molecule.

In some embodiments, a given one of said second subset of nucleotide analogs does not comprise a reporter moiety. In some embodiments, said given one of said second subset of nucleotide analogs comprises a quencher.

In some embodiments, said given one of said second subset of nucleotide analogs has structural homology of 85% or more with respect to said given one of said first subset of nucleotide analogs.

In some embodiments, said nucleotide mixture further comprises naturally occurring nucleotides. In some embodiments, said naturally occurring nucleotides are selected from the group consisting of adenine-containing nucleotides, thymine-containing nucleotides, cytosine-containing nucleotides, guanine-containing nucleotides, and uracil-containing nucleotides.

In some embodiments, said reporter moiety is a fluorophore.

In some embodiments, during incorporation, said given one of said first subset of nucleotide analogs and said given one of said second subset of nucleotide analogs are indistinguishable by an enzyme facilitating said incorporation. In some embodiments, said enzyme is a DNA polymerase. In some embodiments, the enzyme is mutated. In some embodiments, the mutation allows for efficient incorporation of the first subset of nucleotide analogs.

In some embodiments, said first subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, said second subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, the nucleotide mixture further comprises a third subset of nucleotides or nucleotide analogs, wherein none of the third subset of nucleotides or nucleotide analogs comprises a reporter moiety.

In some embodiments, prior to step c), there is an addition of an additive. In some embodiments the additive prevents misincorporation and/or changes incorporation rates. In some embodiments, the additive is betaine, DMSO, formamide, TMAC, Triton X-100, Tween 20, or Nonidet P-40.

In another aspect, the present disclosure provides a method for determining a nucleic acid sequence of a target nucleic acid molecule comprising: (a) providing plurality of nucleic acid molecules immobilized to a support, wherein each of the plurality of nucleic acid molecules exhibits sequence homology to the target nucleic acid molecule, and wherein the support is operatively coupled to a detector; (b) directing a nucleotide mixture to the plurality of nucleic acid molecules immobilized to the support, which nucleotide mixture comprises at least a first subset of nucleotide analogs and a second subset of nucleotide analogs, wherein (i) a given one of the first subset of nucleotide analogs comprises a reporter moiety, (ii) a given one of the second subset of nucleotide analogs comprises a functional analog of the reporter moiety, (iii) the given one of the first subset of nucleotide analogs yields a signal that is detectable by the detector, (iv) the given one of the second subset of nucleotide analogs does not yield a signal that is detectable by the detector, and (v) the given one of the second subset of nucleotide analogs has structural homology of 85% or more with respect to the given one of the first subset of nucleotide analogs; (c) incorporating the nucleotide mixture comprising at least the first subset of nucleotide analogs and the second subset of nucleotide analogs, including the given one of the first subset of nucleotide analogs, into the plurality of nucleic acid molecules; (d) using the detector to detect the signal from the given one of the first subset of nucleotide analogs; and (e) repeating (c) and (d), thereby determining the nucleic acid sequence of the target nucleic acid molecule.

In some embodiments, the nucleotide mixture further comprises naturally occurring nucleotides. In some embodiments, the naturally occurring nucleotides are selected from the group consisting of adenine-containing nucleotides, thymine-containing nucleotides, cytosine-containing nucleotides, guanine-containing nucleotides, and uracil-containing nucleotides.

In some embodiments, the functional analog of the reporter moiety is a quencher.

In some embodiments, the reporter moiety is a fluorophore. In some embodiments, the given one of the first subset of nucleotide analogs comprises the reporter moiety and a first linker moiety. In some embodiments, the first linker moiety is a polymer. In some embodiments, the first linker moiety is a synthetic polymer. In some embodiments, the first linker moiety is a natural polymer. In some embodiments, the first linker moiety comprises a sequence of at least 5 or more nucleotides. In some embodiments, the first linker moiety is subjected to a first stimulus. In some embodiments, the first linker moiety is cleaved after being subjected to said first stimulus. In some embodiments, the first stimulus is chemical. In some embodiments, the first stimulus is enzymatic. In some embodiments, the first stimulus is photochemical.

In some embodiments, during incorporation, the given one of the first subset of nucleotide analogs and the given one of the second subset of nucleotide analogs are indistinguishable by an enzyme facilitating the incorporation. In some embodiments, the enzyme is a DNA polymerase. In some embodiments, the enzyme is mutated. In some embodiments, the mutation allows for efficient incorporation of the first subset of nucleotide analogs.

In some embodiments, the given one of the second subset of nucleotide analogs comprises a second linker moiety. In some embodiments, the second linker moiety is a polymer. In some embodiments, the second linker moiety is a natural polymer. In some embodiments, the second linker moiety is a synthetic polymer. In some embodiments, the second linker moiety comprises a sequence of at least 5 or more nucleotides. In some embodiments, the second linker moiety is subjected to a second stimulus. In some embodiments, the second linker moiety is cleaved after being subjected to the second stimulus. In some embodiments, the second stimulus is chemical. In some embodiments, the second stimulus is enzymatic. In some embodiments, the second stimulus is photochemical.

In some embodiments, the first set of nucleotide analogs and the second set of nucleotide analogs are structured such that a first $K_m$ of a polymerase reaction with the first set of nucleotide analogs and a second $K_m$ for a polymerase reaction with the second set of nucleotide analogs are within 30% of one another.

In some embodiments, the first set of nucleotide analogs and the second set of nucleotide analogs are structured such that a first $K_{cat}$ of a polymerase reaction with the first set of nucleotide analogs and a second $K_{cat}$ for a polymerase reaction with the second set of nucleotide analogs are within 30% of one another.

In some embodiments, the first set of nucleotide analogs and the second set of nucleotide analogs are structured such that a first $V_{max}$ of a polymerase reaction with the first set of nucleotide analogs and a second $V_{max}$ for a polymerase reaction with the second set of nucleotide analogs are within 30% of one another.

In some embodiments, the first subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, the second subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, the nucleotide mixture further comprises a third subset of nucleotides or nucleotide analogs, wherein none of the third subset of nucleotides or nucleotide analogs comprises a reporter moiety.

In a further aspect, the present disclosure provides a system for determining a nucleic acid sequence of a target nucleic acid molecule, comprising: a detector; a support that is configured to immobilize a plurality of nucleic acid molecules, wherein each of said plurality of nucleic acid molecules exhibits sequence homology to said target nucleic acid molecule, and wherein said support is operatively coupled to said detector; and a controller operatively coupled to said detector, wherein said controller comprises one or more computer processors that are individually or collectively programmed to: (a) direct a nucleotide mixture to said plurality of nucleic acid molecules immobilized to said support, which said nucleotide mixture comprises at least a first subset of nucleotide analogs and a second subset of nucleotide analogs, wherein nucleotide analogs of said first subset and said second subset are different from one another, wherein a given one of said first subset of nucleotide analogs comprises a reporter moiety and is detectable by said detector, and wherein a given one of said second subset of nucleotide analogs is not detectable by said detector; (b) permit incorporation of said nucleotide mixture comprising at least said first subset of nucleotide analogs and said second subset of nucleotide analogs into said plurality of nucleic acid molecules; (c) using said detector to detect said signal from said given one of said first subset of nucleotides or nucleotide analogs; and (d) repeating (b) and (c), thereby determining said nucleic acid sequence of said target nucleic acid molecule.

In another aspect, the disclosure provides a system for determining a nucleic acid sequence of a target nucleic acid molecule. The system comprises: a detector; a support that is configured to immobilize a plurality of nucleic acid molecules, wherein each of the plurality of nucleic acid molecules exhibits sequence homology to the target nucleic acid molecule, and wherein the support is operatively coupled to the detector; and a controller operatively coupled to the detector, wherein the controller comprises one or more computer processors that are individually or collectively programmed to: (a) direct a nucleotide mixture to the plurality of nucleic acid molecules immobilized to the support, which nucleotide mixture comprises at least a first subset of nucleotide analogs and a second subset of nucleotide analogs, wherein (i) a given one of the first subset of nucleotide analogs comprises a reporter moiety, (ii) a given one of the second subset of nucleotide analogs comprises a functional analog of the reporter moiety, (iii) the given one of the first subset of nucleotide analogs yields a signal that is detectable by the detector, (iv) the given one of the second subset of nucleotide analogs does not yield a signal that is detectable by the detector, and (v) the given one of the second subset of nucleotide analogs has structural homology of 85% or more with respect to the given one of the first subset of nucleotide analogs; (b) permit incorporation of the nucleotide mixture comprising at least the first subset of nucleotide analogs and the second subset of nucleotide analogs, including the given one of the first subset of nucleotide analogs, into the plurality of nucleic acid molecules; (c) using the detector to detect the signal from the given one of the first subset of nucleotide analogs; and (d) repeating (b) and (c), thereby determining the nucleic acid sequence of the target nucleic acid molecule.

In another aspect, the present disclosure provides a non-transitory computer-readable medium comprising machine-executable code that, upon execution by one or more computer processors, implements a method for determining a nucleic acid sequence of a target nucleic acid molecule, said method comprising: (a) providing plurality of nucleic acid molecules immobilized to a support, wherein each of said plurality of nucleic acid molecules exhibits sequence homology to said target nucleic acid molecule, and wherein said support is operatively coupled to a detector; (b) directing a nucleotide mixture to said plurality of nucleic acid molecules immobilized to said support, which said nucleotide mixture comprises at least a first subset of nucleotide analogs and a second subset of nucleotide analogs, wherein nucleotide analogs of said first subset and said second subset are different from one another, wherein a given one of said first subset of nucleotide analogs comprises a reporter moiety and is detectable by said detector, and wherein a given one of said second subset of nucleotide analogs is not detectable by said detector; (c) incorporating said nucleotide mixture comprising at least said first subset of nucleotide analogs and said second subset of nucleotide analogs into said plurality of nucleic acid molecules; (d) using said detector to detect said given one of said first subset of nucleotide analogs; and (e) repeating (c) and (d), thereby determining said nucleic acid sequence of said target nucleic acid molecule.

An additional aspect of the disclosure comprises a non-transitory computer-readable medium comprising machine-executable code that, upon execution by one or more computer processors, implements a method for determining a nucleic acid sequence of a target nucleic acid molecule. The method comprises: (a) providing plurality of nucleic acid molecules immobilized to a support, wherein each of the plurality of nucleic acid molecules exhibits sequence homology to the target nucleic acid molecule, and wherein the support is operatively coupled to a detector; (b) directing a nucleotide mixture to the plurality of nucleic acid molecules immobilized to the support, which nucleotide mixture comprises at least a first subset of nucleotide analogs and a second subset of nucleotide analogs, wherein (i) a given one of the first subset of nucleotide analogs comprises a reporter moiety, (ii) a given one of the second subset of nucleotide analogs comprises a functional analog of the reporter moiety, (iii) the given one of the first subset of nucleotide analogs yields a signal that is detectable by the detector, (iv) the given one of the second subset of nucleotide analogs does not yield a signal that is detectable by the detector, and (v) the given one of the second subset of nucleotide analogs has structural homology of 85% or more with the given one of the first subset of nucleotide analogs; (c) incorporating the nucleotide mixture comprising the first subset of nucleotide analogs and the second subset of nucleotide analogs, including the given one of the first subset of nucleotide analogs, into the plurality of nucleic acid molecules; (d) using the detector to detect the signal from the given one of the first subset of nucleotide analogs, and (e) repeating (c) and (d), thereby determining the nucleic acid sequence of the target nucleic acid molecule.

In another aspect, provided is a method for analyzing a target nucleic acid molecule, comprising (i) bringing the target nucleic acid molecule immobilized to a support in contact with a nucleotide mixture comprising a first set of nucleotide analogs and a second set of nucleotide analogs, wherein nucleotide analogs of the first set and nucleotide analogs of the second set are different nucleotide analogs but of the same canonical base type, and wherein nucleotide analogs of the first set or the second set, but not both, are detectable, and (ii) detecting one or more signals from the target nucleic acid molecule, thereby determining at least a portion of the nucleic acid sequence.

In some embodiments, a sum of the first set of nucleotide analogs and the second set of nucleotide analogs is at least 80% of the nucleotide mixture. In some embodiments, the sum is at least 97% of the nucleotide mixture.

In some embodiments, the nucleotide mixture further comprises naturally occurring nucleotides. In some embodiments, the naturally occurring nucleotides are selected from the group consisting of adenine-containing nucleotides, thymine-containing nucleotides, cytosine-containing nucleotides, guanine-containing nucleotides, and uracil-containing nucleotides.

In some embodiments, a first given nucleotide analog of the first set of nucleotide analogs has structural homology of 85% or more with respect to a second given nucleotide analog of the second set of nucleotide analogs.

In some embodiments, a first given nucleotide analog of the first set of nucleotide analogs comprises a first reporter moiety and wherein a second given nucleotide analog of the second set of nucleotide analogs comprises a second reporter moiety different from the first reporter moiety.

In some embodiments, the one or more signals are detected from nucleotide analogs from the first set of nucleotide analogs. In some embodiments, the one or more signals are detected only from nucleotide analogs from the first set of nucleotide analogs.

In some embodiments, during incorporation of the nucleotide analogs of the first set and the nucleotide analogs of the second set to the target nucleic acid molecule, a first given nucleotide analog of the first set of nucleotide analogs and a second given nucleotide analog of the second set of nucleotide analogs are indistinguishable by an enzyme facilitating the incorporation. In some embodiments, the enzyme is a DNA polymerase. In some embodiments, the enzyme is mutated.

In some embodiments, the first set of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, the second set of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

In some embodiments, the nucleotide mixture further comprises a third set of nucleotides or nucleotide analogs, wherein none of the third set of nucleotides or nucleotide analogs comprises a reporter moiety.

In some embodiments, the method further comprises introducing an additive prior to (ii). In some embodiments, the additive prevents misincorporation. In some embodiments, the additive changes incorporation rates. In some embodiments, the additive is selected from a group consisting of betaine, DMSO, formamide, TMAC, Triton X-100, Tween 20, and Nonidet P-40.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by references to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 tabulates data obtained from various experiments in Example 6;

FIG. 7 shows the results of the homopolymer assay of Example 9; FIG. 7 discloses SEQ ID NOS 1, 2 and 2, respectively, in order of appearance;

FIG. 8 discloses SEQ ID NOS 3, 8, 4, 3, 9, 5, 3 10, 6, 7 and 11, respectively, in order of appearance.

DETAILED DESCRIPTION

Figure 1:
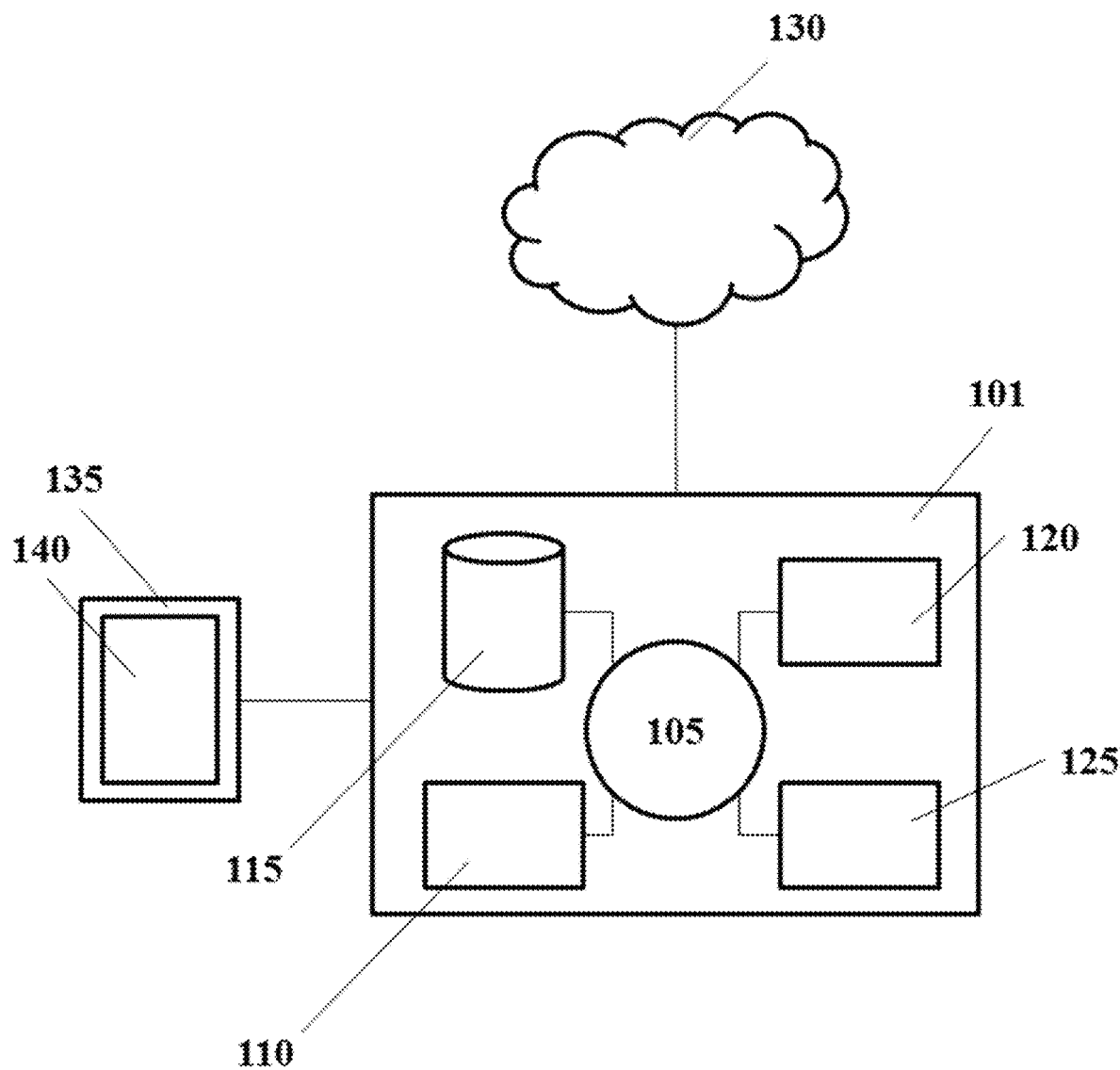
FIG. 1 shows a computer control system that is programmed or otherwise configured to implement methods or systems provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terms "amplifying," "amplification," and "nucleic acid amplification" are used interchangeably and generally refer to generating one or more copies of a nucleic acid. For example, "amplification" of deoxyribonucleic acid (DNA) generally refers to generating one or more copies of a DNA molecule. Moreover, amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, mini-primer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C. C. PNAS, 1989, 86, 4076-4080 and U.S. Pat. Nos. 5,409,811 and 5,674,716, each of which is herein incorporated by reference in its entirety.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP), and deoxythymidine triphosphate (dTTP). A nucleotide such as a dNTP may include one or more detectable tags, such as luminescent tags or markers (e.g., fluorophores). A nucleotide can include any subunit that can be incorporated into a growing nucleic acid strand. Such subunit can be an A, C, G, T, or U, or any other subunit that is specific or complementary to one or more such subunits, such as a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths and may comprise subunits such as deoxyribonucleotides or ribonucleotides (RNA), or analogs thereof. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" and related terms refer to the alphabetical representation of a polynucleotide molecule; alternatively, such terms may be applied to the polynucleotide molecule itself. This alphabetical representation can be inputted into databases in a computer having a central processing unit and used for bio-informatics applications such as functional genomics and homology searching. Oligonucleotides may include one or more nonstandard or non-natural nucleotide(s), nucleotide analog(s) and/or modified nucleotide(s).

The term "nucleotide mixture," as used herein, generally refers to a collection of nucleotide molecules. Nucleotide molecules of a nucleotide mixture may be naturally occurring nucleotide molecules and/or derivatives, analogs, or modified versions thereof. The terms "nucleotide molecule" and "nucleotide" may be used interchangeably herein. A nucleotide mixture may comprise one or more subsets of nucleotide molecules. For example, a nucleotide mixture may comprise one or more subsets of nucleotide analogs and/or one or more subsets of naturally occurring nucleotide molecules. A nucleotide mixture may comprise any number of subsets of nucleotide molecules. For example, a nucleotide mixture may comprise 1, 2, 3, 4, 5, 6, 7, 8, 9, 10, or more subsets of nucleotide molecules. A plurality of subsets of nucleotide molecules in the nucleotide mixture may be of the same type of nucleotide molecules or be different types of nucleotide molecules. Nucleotide molecules of a given subset of a nucleotide mixture may share one or more characteristics. For example, the nucleotide molecules of the given subset may each comprise a feature such as a reporter moiety. In another example, the nucleotide molecules of the given subset may each lack a reporter moiety. Alternatively or in addition, the nucleotide molecules of a given subset of a nucleotide mixture may have one or more shared structural features. In some cases, nucleotide molecules of a subset of a nucleotide mixture may have the same nucleobase (e.g., adenine, guanine, cytosine, thymine, or uracil). In an example, a nucleotide mixture may comprise a first subset of nucleotide molecules and a second subset of nucleotide molecules, where the nucleotide molecules of the first and second subsets comprise the same nucleobase, and where nucleotide molecules of the first subset comprise a reporter moiety and nucleotide molecules of the second subset do not comprise a reporter moiety.

Examples of modified nucleotides include, but are not limited to diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thio triphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes.

The term "sequencing," as used herein, generally refers to generating or identifying a sequence of a biological molecule, such as a nucleic acid molecule. Sequencing may comprise single molecule sequencing or sequencing by synthesis. Sequencing may comprise massively parallel array sequencing (e.g., Illumina sequencing), which may be performed using template nucleic acid molecules immobilized on a support, such as a flow cell or beads.

The term "polymerase," as used herein, generally refers to any enzyme capable of catalyzing a polymerization reaction. Examples of polymerases include, without limitation, a nucleic acid polymerase. The polymerase can be naturally occurring or synthesized. In some cases, a polymerase has relatively high processivity. An example polymerase is a Φ29 polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such, as for example, Sequenase DNA polymerase (ThermoFisher).

The term "sample," as used herein, generally refers to a biological sample. Examples of biological samples include nucleic acid molecules, amino acids, polypeptides, proteins, carbohydrates, fats, or viruses. In some cases, the sample contains a target nucleic acid molecule. In an example, a biological sample is a nucleic acid sample including one or more nucleic acid molecules. In some examples, the biological sample is a nucleic acid sample including one or more target nucleic acid molecules. The target nucleic acid molecules may be cell-free or cell-free nucleic acid molecules, such as cell free DNA or cell free RNA. The target nucleic acid molecules may be derived from a variety of sources including, but not limited to, human, mammal, non-human mammal, ape, monkey, chimpanzee, reptilian, amphibian, and avian sources. Further, samples may be extracted from a variety of animal fluids containing cell free sequences, including, but not limited to, blood, serum, plasma, vitreous, sputum, urine, tears, perspiration, saliva, semen, mucosal excretions, mucus, spinal fluid, amniotic fluid, lymph fluid, and the like. Cell free polynucleotides may be fetal in origin (via fluid taken from a pregnant subject), or may be derived from tissue of the subject itself.

The term "mutation" or "mutated" as used herein generally refers to genetic mutations or sequence variations such as point mutations, single nucleotide polymorphisms ("SNPs"), insertions, deletions, substitutions, transpositions, translocations, copy number variations, and other genetic mutations, alterations, and/or sequence variations.

The term "support" as used herein generally refers to a solid or semi-solid support such as a slide, a bead, a resin, a chip, an array, a matrix, a membrane, a nanopore, or a gel. The solid support may, for example, be a bead on a flat substrate (such as glass, plastic, silicon, etc.) or a bead within a well of a substrate. The substrate may have surface properties, such as textures, patterns, microstructure coatings, surfactants, or any combination thereof to retain the bead at a desired location (such as in a position to be in operative communication with a detector). The detector of bead-based supports may be configured to maintain substantially the same read rate independent of the size of the bead. The support may be a flow cell or an open substrate. Furthermore, the support may comprise a biological support, a non-biological support, an organic support, an inorganic support, or any combination thereof. The support may be in optical communication with the detector, may be physically in contact with the detector, may be separated from the detector by a distance, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. The support may be optically coupled to the detector. Immobilization on the support may be aided by an adaptor.

The term "detector" as used herein generally refers to a device, generally including optical and/or electronic components that can detect signals.

The term "reporter moiety" as used herein, generally refers to a moiety that emits a signal that can be detected. In some cases, such a signal may be indicative of incorporation of one or more nucleotides or nucleotide analogs. In some cases, a reporter moiety is coupled to a nucleotide or nucleotide analog, which nucleotide or nucleotide analog may be used in a primer extension reaction. Coupling may be covalent or non-covalent (e.g., via ionic interactions, Van der Waals forces, etc.). Where covalent coupling is implemented, the reporter moiety may be coupled to the nucleotide or nucleotide analog via a linker, with non-limiting examples that include aminopropargyl, aminoethoxypropargyl, polyethylene glycol, polypeptides, fatty acid chains, hydrocarbon chains and disulfide linkages. In some cases, the linker is cleavable, such as photo-cleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase or protease). In some cases, the linker is non-cleavable.

In some examples, the reporter moieties comprise molecular structures that, once attached to a nucleic acid sequence, provide a distinct characteristic that is not inherent to those nucleic acid molecules. In some cases the reporter moieties create unique optical characteristics. In some cases, the reporter moieties can be used as a single signal generating entity or may be one of a pair of reporter moieties such that one reporter moiety performs the role of an energy donor, and the other reporter moiety performs the role of energy acceptor. Energy donors and/or energy acceptors can both be fluorophore molecules. Whether a fluorophore is a donor or an acceptor may be based on its excitation and emission spectra, and the fluorophore with which it is paired.

Examples of energy donor/energy acceptor fluorophore pairs include, but are not limited to, cyan fluorescent protein (CFP) and yellow fluorescent protein (YFP); Cy3 and Cy5; fluorescein and tetramethylrhodamine; IAEDANS and fluorescein; EDANS and dabcyl; fluorescein and QSY 7 or QSY 9 dyes; Alex Fluor 350 and Alexa Fluor 488; Alexa Fluor 488 and Alexa Fluor 546, 555, 568, 594, or 647; Alexa Fluor 568 and Alexa Fluor 647; and Alexa Fluor 594 and Alexa Fluor 85.

The term "quencher," as used herein, generally refers to molecules that may be energy acceptors. Quencher molecules can be used with in some cases of the present method disclosed herein as acceptors of a dual reporter moiety structure. Example quenchers, without limitation, include Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare). Examples of fluorophore donor molecules that can be used in conjunction with above quenchers include, without limitation, fluorophores such as Cy3B, Cy3, or Cy5; Dy-Quenchers (Dyomics), such as DYQ-660 and DYQ-661; and ATTO fluorescent quenchers (ATTO-TEC GmbH), such as ATTO 540Q, 580Q, 612Q.

The term "nucleotide analog," as used herein, generally refers to an unnatural or non-naturally occurring nucleotide. A nucleotide analog may be detectable or undetectable. Examples of nucleotides and nucleotide analogs include, but are not limited to, thymidine triphosphate (TTP), deoxythymidine triphosphate (dTTP), deoxyuridine triphosphate (dUTP), 5-propynyl-2'-deoxyuridine 5'triphosphate (5-propynyl-dUTP), 5-bromo-2'-deoxyuridine 5'triphosphate (5-bromo-dUTP), 5-iodo-2'-deoxyuridine 5'triphosphate (5-iodo-dUTP), 5-ethynyl-2'-deoxyuridine 5'triphosphate (5-ethynyl-dUTP), 5-fluoro-2'-deoxyuridine 5'triphosphate (5-fluoro-dUTP), 5-proparylamino-2'-deoxyuridine 5'triphosphate (5-proparylamino-dUTP), 5-(oct-1,7-diynyl)-2'-deoxyuridine 5'triphosphate (5-octynyl-dUTP), deoxycytidine triphosphate (dCTP), 5-methyl-2'-deoxycytidine 5'triphosphate (5-methyl-dCTP), 5-bromo-2'-deoxycytidine 5'triphosphate (5-bromo-dCTP), 5-propynyl-2'-deoxycytidine 5'triphosphate (5-propynyl-dCTP), 5-ethynyl-2'-deoxycytidine 5'triphosphate (5-ethynyl-dCTP), 5-hydroxy-2'-deoxycytidine 5'triphosphate (5-hydroxy-dCTP), 5-ydroxymethyl-2'-deoxycytidine 5'triphosphate (5-hydroxymethyl-dCTP), 5-formyl-2'-deoxycytidine 5'triphosphate (5-formyl-dCTP), deoxyadenosine triphosphate (dATP), bromo-deoxyadenosine triphosphate, 7-deaza-7-iodo-2'-deoxyadenosine-5'-triphosphate (7-deaza-7-iodo-dATP), 7-deaza-2'-deoxyadenosine-5'-triphosphate (7-deaza-dATP), deoxyguanosine triphosphate (dGTP), iodo-2'-deoxyguanosine-5'-triphosphate (iodo-dGTP), 7-deaza-2'-deoxyguanosine-5'-triphosphate (7-deaza-dGTP), 5-Bromo-2'-deoxycytidine-5'-Triphosphate, 5-Propynyl-2'-deoxycytidine-5'-Triphosphate, 5-Ethynyl-2'-deoxycytidine-5'-Triphosphate, 5-Iodo-2'-deoxycytidine-5'-Triphosphate, 5-Methyl-2'-deoxycytidine-5'-Triphosphate, 5-Hydroxy-2'-deoxycytidine-5'-Triphosphate, 5-Aminoallyl-2'-deoxycytidine-5'-Triphosphate, 5-Hydroxymethyl-2'-deoxycytidine-5'-Triphosphate, 5-Propargylamino-2'-deoxycytidine-5'-Triphosphate, 5-Carboxy-2'-deoxycytidine-5'-Triphosphate, 5-Formyl-2'-deoxycytidine-5'-Triphosphate, 5-Bromo-2'-deoxyuridine-5'-Triphosphate, 5-Propynyl-2'-deoxyuridine-5'-Triphosphate, 5-Ethynyl-2'-deoxyuridine-5'-Triphosphate, 5-Iodo-2'-deoxyuridine-5'-Triphosphate, 5-Methyl-2'-deoxyuridine-5'-Triphosphate, 5-Hydroxy-2'-deoxyuridine-5'-Triphosphate, 5-Aminoallyl-2'-deoxyuridine-5'-Triphosphate, 5-Hydroxymethyl-2'-deoxyuridine-5'-Triphosphate, 5-Propargylamino-2'-deoxyuridine-5'-Triphosphate, 5-Carboxy-2'-deoxyuridine-5'-Triphosphate, 5-Formyl-2'-deoxyuridine-5'-Triphosphate, 7-deaza-7-Bromo-2'-deoxyguanosine-5'-Triphosphate, 7-deaza-7-Propynyl-2'-deoxyguanosine-5'-Triphosphate, 7-deaza-7-Ethynyl-2'-deoxyguanosine-5'-Triphosphate, 7-deaza-7-Iodo-2'-deguanosine-5'-Triphosphate, 7-deaza-7-Methyl-2'-deoxyguanosine-5'-Triphosphate, 7-deaza-7-Hydroxy-2'-deoxyguanosine-5'-Triphosphate, 7-deaza-7-Aminoallyl-2'-deoxyguanosine-5'-Triphosphate, 7-deaza-7-Hydroxymethyl-2'-deoxyguanosine-5'-Triphosphate, 7-deaza-7-Propargylamino-2'-deoxyguanosine-5'-Triphosphate, 7-deaza-7-carboxy-2'-deoxyguanosine-5'-Triphosphate, 7-deaza-7-Formyl-2'-deoxyguanosine-5'-Triphosphate, 7-deaza-7-Bromo-2'-deoxyadenosine-5'-Triphosphate, 7-deaza-7-Propynyl-2'-deoxyadenosine-5'-Triphosphate, 7-deaza-7-Ethynyl-2'-deoxyadenosine-5'-Triphosphate, 7-deaza-7-Iodo-2'-deoxyadenosine-5'-Triphosphate, 7-deaza-7-Methyl-2'-deoxyadenosine-5'-Triphosphate, 7-deaza-7-Hydroxy-2'-deoxyadenosine-5'-Triphosphate, 7-deaza-7-Aminoallyl-2'-deoxyadenosine-5'-Triphosphate, 7-deaza-7-Hydroxymethyl-2'-deoxyadenosine-5'-Triphosphate, 7-deaza-7-Propargylamino-2'-deoxyadenosine-5'-Triphosphate, 7-deaza-7-carboxy-2'-deoxyadenosine-5'-Triphosphate, and 7-deaza-7-Formyl-2'-deoxyadenosine-5'-Triphosphate.

In some cases, nucleotide molecules of a subset of nucleotide molecules of a nucleotide mixture may not be detectable by a detector. For example, in the case of an optical detector that collects optical signals, non-detectable nucleotide molecules may not comprise a dye, fluorophore, or other moiety (e.g., reporter moiety) that may render a nucleotide molecule detectable. In another example, nucleotide molecules of a subset of nucleotide molecules of a nucleotide mixture may emit a signal. However this signal may be below the detectable threshold of a detector.

In some examples, reporter moieties may be nucleic acid intercalator dyes. Examples include, but are not limited to ethidium bromide, YOYO-1, SYBR Green, and EvaGreen. The near-field interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Förster resonance energy transfer (FRET) (i.e., energy transfer from the donor to an acceptor that results in radiative energy decay).

Other examples of reporter moieties include electrochemical labels, electrostatic labels, colorimetric labels, and mass tags. Such labels may be used with the systems and methods disclosed herein.

Methods

The present disclosure provides methods for determining a nucleic acid sequence of a target nucleic acid molecule. The methods may comprise incorporating bases that are complementary to a sequence of the target nucleic acid molecule. Such incorporation may be performed by using an enzyme, such as, for example, a polymerase. In some cases, at least two sets of nucleotides (e.g., naturally occurring nucleotides or nucleotide analogs) are used. Nucleotides from a first set and nucleotides from a second set of the at least two sets of nucleotides may be indistinguishable in one or more ways (e.g., structurally or chemically indistinguishable) from one another, but nucleotides from the first set may yield a detectable signal upon, during, or after incorporation, and nucleotides from the second set may not yield a detectable signal. The methods described herein may address issues with nucleotide misincorporation during sequencing.

In an aspect, disclosed herein is a method for determining a nucleic acid sequence of a target nucleic acid molecule. The method may comprise providing a plurality of nucleic acid molecules immobilized to a support. Each of the plurality of nucleic acid molecules may exhibit sequence homology to the target nucleic acid molecule. In some examples, the support may be operatively coupled to a detector.

Sequence homology between a first nucleic acid sequence and a second nucleic acid sequence may refer to the identity or substantial identity between the first nucleic acid sequence and the second nucleic acid sequence. Sequence homology may refer to a shared ancestry between the two sequences.

The method may comprise directing a plurality of nucleotides or nucleotide analogs to the plurality of nucleic acid molecules immobilized to the support. The plurality of nucleotides or nucleotide analogs may comprise at least a first subset of nucleotides or nucleotide analogs and a second subset of nucleotides or nucleotide analogs. A given one of the first subset of nucleotides or nucleotide analogs and a given one of the second subset of nucleotides or nucleotide analogs may be structurally or chemically similar to, or indistinguishable from, one another, such as with respect to enzymatic activity (e.g., polymerase activity). In some examples, a given one of the first subset of nucleotides or nucleotide analogs may comprise a reporter moiety, and a given one of the second subset of nucleotides or nucleotide analogs may comprise another reporter moiety or functional analog thereof. In particular, the functional analog may reduce the amount of misincorporation that can arise in stepwise sequencing. In some cases, the functional analog may reduce the amount of misincorporation that occurs in homopolymers.

The term "functional analog," as used herein, generally refers to a moiety that is functionally equivalent to another moiety but does not share all of the features of the other moiety. For example, a functional analog of a reporter moiety that comprises a fluorophore may not comprise a fluorophore but may have steric and/or electrostatic features that allow the functional analog to interact with an enzyme (e.g., a polymerase) in a manner similar to the way the reporter moiety interacts with the enzyme. The reporter moiety and the functional analog thereof may be chemically indistinguishable, and/or may have similar charges, similar atomic weights, similar diffusion speeds, similar chemical compositions, and/or other similarities. Accordingly, such a functional analog may facilitate incorporation of nucleotides at a given location on a given template nucleic acid molecule.

In the method, the given one of the first subset of nucleotides or nucleotide analogs may yield a signal that is detectable by the detector. In some cases, the given one of the second subset of nucleotides or nucleotide analogs may not yield a signal that is detectable by the detector. For example, the given one of the second subset of nucleotides or nucleotide analogs may yield a signal but the detector may not be configured to detect the signal. In some cases, a wavelength selector such as a filter, block, waveplate, or other device may be used to prevent the detector from detecting the signal. In some cases, the detector may not be sensitive to a signal yielded by the given one of the second subset of nucleotides or nucleotide analogs. For example, the detector may not be sensitive to a signal at a particular wavelength or range of wavelengths. In some cases, the given one of the second subset of nucleotides or nucleotide analogs may not yield a signal at all.

In some examples, a given one of the second subset of nucleotides or nucleotide analogs may have structural homology of at least 50%, 60%, 70%, 80%, 85%, 90%, 95% or more with respect to a given one of the first subset of nucleotides or nucleotide analogs. For example, the given one of the second subset of nucleotides or nucleotide analogs may have structural homology of at least 85% with respect to the given one of the first subset of nucleotides or nucleotide analogs. The term "structural homology" generally refers to the degree of three dimensional shape similarities between nucleotides, such as between a nucleotide of the second subset and a nucleotide of the first subset.

The method may include the incorporation of all or a portion of the plurality of nucleotides or nucleotide analogs comprising the first subset of nucleotides or nucleotide analogs and the second subset of nucleotides or nucleotide analogs. In particular, the given one of the first subset of nucleotides or nucleotide analogs may be incorporated into the plurality of nucleic acid molecules.

The method may use a detector to detect the signal from the given one of the first subset of nucleotides or nucleotide analogs. By sequentially repeating the steps of incorporation and detection, the nucleic acid sequence of the target nucleic acid molecule may be determined.

In an example, the present disclosure provides a method for determining a nucleic acid sequence of a target nucleic acid molecule comprising providing a plurality of nucleic acid molecules immobilized to a support, wherein each of the plurality of nucleic acid molecules exhibits sequence homology to the target nucleic acid molecule. The support may be operatively coupled to a detector. A nucleotide mixture may then be directed to the plurality of nucleic acid molecules immobilized to the support. The nucleotide mixture may comprise at least a first subset of nucleotide analogs and a second subset of nucleotide analogs, wherein nucleotide analogs of the first subset and the second subset are different from one another. A given one of the first subset of nucleotide analogs may comprise a reporter moiety and be detectable by said detector (e.g., upon incorporation into a nucleic acid molecule), and a given one of the second subset of nucleotide analogs may not be detectable by said detector (e.g., because it does not yield a detectable signal or because the detector is not configured to detect a signal yielded by the nucleotide analog). The nucleotide mixture may be incorporated into the plurality of nucleic acid molecules. The detector may be used to detect a signal associated with the given one of the first subset of nucleotide analogs. The incorporation and detection processes may be repeated one or more times, thereby determining the nucleic acid sequence of the target nucleic acid molecule.

In some cases, the reporter moiety and/or another reporter moiety may be fluorophores. In some cases, the given one of the first subset of nucleotides or nucleotide analogs and/or the given one of the second subset of nucleotides or nucleotide analogs may comprise a quencher. In some examples, the reporter moiety on a given one of the first subset of nucleotides and the reporter moiety on a given one of the second subset of nucleotides are identical. In some examples, the reporter moiety on a given one of the first subset of nucleotides and the reporter moiety on a given one of the second subset of nucleotides are not identical.

In some examples, during incorporation, the given one of the first subset of nucleotides or nucleotide analogs and the given one of the second subset of nucleotides or nucleotide analogs are indistinguishable by an enzyme facilitating the incorporation. The term "indistinguishable," as used herein, generally means that the given one of the first subset of nucleotides or nucleotide analogs and the given one of the second subset of nucleotides or nucleotide analogs may have similar charges, similar atomic weights, similar diffusion speeds, similar chemical compositions, or other similarities.

In some cases, the enzyme facilitating the incorporation may be a DNA polymerase. In some examples, the first set of nucleotides or nucleotide analogs and the second set of nucleotides or nucleotide analogs are structured such that a first $K_m$ (Michaelis constant) of a polymerase reaction with the first set of nucleotides or nucleotide analogs and a second $K_m$ for a polymerase reaction with the second set of nucleotides or nucleotide analogs are within 30% of one another. In some examples, the first set of nucleotides or nucleotide analogs and the second set of nucleotides or nucleotide analogs are structured such that a first $K_{cat}$ (catalyst rate constant) of a polymerase reaction with the first set of nucleotides or nucleotide analogs and a second $K_{cat}$ for a polymerase reaction with the second set of nucleotides or nucleotide analogs are within 30% of one another. In some examples, the first set of nucleotides or nucleotide analogs and the second set of nucleotides or nucleotide analogs are structured such that a first $V_{max}$ (maximal rate of reaction) of a polymerase reaction with the first set of nucleotides or nucleotide analogs and a second $V_{max}$ for a polymerase reaction with the second set of nucleotides or nucleotide analogs are within 30% of one another. Generally, the term "$K_m$" as used herein refers to the Michaelis constant which is a measure of the substrate concentration required for effective catalysis to occur. The Michaelis-Menten equation is $V=V_{max}[S]/(K_m+[S])$ which may be rewritten as $V=K_{cat}[E]_t[S]/(K_m+[S])$, where [S] is the substrate concentration, and [E] is the enzyme concentration.

The enzyme may be mutated and in some examples, the mutation may allow for the efficient incorporation of the first subset of nucleotides or nucleotide analogs and the second subset of nucleotides or nucleotide analogs.

Moreover, competition between various subsets of nucleotides or nucleotide analogues for incorporation into a plurality of nucleic acid molecules may improve incorporation of a particular subset when compared to the case where the particular subset competes with a subset different from any of the various subsets. For example, competition between a first subset of nucleotides or nucleotide analogs and a second subset of nucleotides or nucleotide analogs for incorporation into a plurality of nucleic acid molecules may improve incorporation of the first subset of nucleotides or nucleotide analogs into the plurality of nucleic acid molecules over the case in which the first subset of nucleotides or nucleotide analogs competes with a third subset of nucleotides or nucleotide analogues different from the second subset of nucleotides or nucleotide analogues for incorporation into the plurality of nucleic acid molecules. In some cases, the third subset of nucleotides or nucleotide analogues comprises a naturally-occurring nucleobase (e.g. adenine, thymine, cytosine, guanine, and uracil). In some cases, the naturally-occurring nucleobase is unmodified. In some cases, the third subset may comprise more than one type of naturally-occurring nucleobase. In some examples, the rate of incorporation of unnatural nucleotides is unexpectedly greater than the rate of incorporation of natural nucleotides.

In some cases, the first subset of nucleotides or nucleotide analogs may be deoxyadenosine-based, dideoxyadenosine-based, deoxythymidine-based, dideoxythymidine-based, deoxyguanosine-based, dideoxyguanosine-based, deoxycytidine-based, or dideoxycytidine-based nucleotides or nucleotide analogs. In some cases, the first subset of nucleotides or nucleotide analogs may comprise at least one, at least two, at least three, at least four, or more nucleotides or nucleotide analogs selected from the group consisting of deoxyadenosine-based, dideoxyadenosine-based, deoxythymidine-based, dideoxythymidine-based, deoxyguanosine-based, dideoxyguanosine-based, deoxycytidine-based, and dideoxycytidine-based nucleotides or nucleotide analogs.

In some examples, the given one of the first subset of nucleotides or nucleotide analogs may comprise the reporter moiety and a first linker moiety. The first linker moiety may be a polymer, such as a natural polymer or synthetic polymer. The first linker moiety may be a sequence of at least 1, 2, 3, 4, 5, 6, 7, 8, 9, 10, 20, 30, 40, 50, 100, or more nucleotides. The first linker moiety may be a polymer of repeating units. In some examples, the first linker may be comprised of 1, 2, 3, 4, 5, 6, 7, 8, 9, 10, 20, 30, 40, 50, 600, or more repeating units. The first linker moiety may be a PEG chain of repeating units. In some examples, the first linker may be comprised of 1, 2, 3, 4, 5, 6, 7, 8, 9, 10, 20, 30, 40, 50, 600, or more repeating units.

In some examples, the first linker moiety may be subjected to a first stimulus. The first linker moiety may be cleaved after being subjected to the first stimulus. In some cases, the first stimulus may be chemical, enzymatic, and/or photochemical.

In some examples, the second subset of nucleotides or nucleotide analogs may be adenosine-based, thymidine-based, guanosine-based, or cytidine-based nucleotides or nucleotide analogs. In some cases the second subset of nucleotides or nucleotide analogs may comprise at least one, at least two, at least three, or more nucleotides or nucleotide analogs selected from the group consisting of adenosine-based, thymidine-based, guanosine-based, and cytidine-based nucleotides or nucleotide analogs. In some cases, the second subset of nucleotides or nucleotide analogs may comprise adenosine-based nucleotides or nucleotide analogs. In some cases, the second subset of nucleotides or nucleotide analogs may comprise thymidine-based nucleotides or nucleotide analogs. In some cases, the second subset of nucleotides or nucleotide analogs may comprise guanosine-based nucleotides or nucleotide analogs. In some cases, the second subset of nucleotides or nucleotide analogs may comprise cytidine-based nucleotides or nucleotide analogs. In some cases, the second subset of nucleotides or nucleotide analogs may comprise both adenosine-based and thymidine-based nucleotides or nucleotide analogs. In some cases, the second subset of nucleotides or nucleotide analogs may comprise both adenosine-based and guanidine-based nucleotides or nucleotide analogs. In some cases, the second subset of nucleotides or nucleotide analogs may comprise both adenosine-based and cytidine-based nucleotides or nucleotide analogs. In some cases, the second subset of nucleotides or nucleotide analogs may comprise both thymidine-based and guanidine-based nucleotides or nucleotide analogs. In some cases, the second subset of nucleotides or nucleotide analogs may comprise both thymidine-based and cytidine-based nucleotides or nucleotide analogs. In some cases, the second subset of nucleotides or nucleotide analogs may comprise both cytidine-based and guanidine-based nucleotides or nucleotide analogs. In some cases, the second subset of nucleotides or nucleotide analogs may comprise adenosine-based, guanidine-based, and thymidine-based nucleotides or nucleotide analogs. In some cases, the second subset of nucleotides or nucleotide analogs may comprise adenosine-based, guanidine-based, and cytidine-based nucleotides or nucleotide analogs. In some cases, the second subset of nucleotides or nucleotide analogs may comprise cytidine-based, guanidine-based, and thymidine-based nucleotides or nucleotide analogs. In some cases, the second subset of nucleotides or nucleotide analogs may comprise adenosine-based, cytidine-based, and thymidine-based nucleotides or nucleotide analogs. In some cases, the second subset of nucleotides or nucleotide analogs may comprise adenosine-based, cytidine-based, guanidine-based, and thymidine-based nucleotides or nucleotide analogs.

In some examples, any one of the adenosine-based, the thymidine-based, the guanosine-based, or the cytidine-based nucleotides or nucleotide analogs present in the second subset of nucleotides or nucleotide analogs may have similar or different modifications compared to the rest of the nucleotide or nucleotide analogs present in the second subset of nucleotides or nucleotide analogs. For example, a first type of nucleotide or nucleotide analog may comprise a first modification and a second type or nucleotide or nucleotide analog may comprise a second modification, where the second modification is different from the first modification. In some cases, a third type of nucleotide or nucleotide analog may comprise a third modification, where the third modification is the same as the first modification. For example, the first and third types of nucleotides or nucleotide analogs may comprise the same reporter moiety, while the first and second types of nucleotides or nucleotide analogs may comprise different reporter moieties, or the first type of nucleotide or nucleotide analog may comprise a reporter moiety and the second type or nucleotide or nucleotide analog may not comprise a reporter moiety.

In some examples, the given one of the second subset of nucleotides or nucleotide analogs may comprise the reporter moiety and a second linker moiety. The second linker moiety may be a polymer, such as a natural polymer or a synthetic polymer. The second linker moiety may be a sequence of at least 1, 2, 3, 4, 5, 6, 7, 8, 9, 10, 20, 30, 40, 50, 100, or more nucleotides. The second linker moiety may be a polymer of repeating units. In some examples, the second linker may be comprised of 1, 2, 3, 4, 5, 6, 7, 8, 9, 10, 20, 30, 40, 50, 600, or more repeating units. The second linker moiety may be a PEG chain of repeating units. In some examples, the second linker may be comprised of 1, 2, 3, 4, 5, 6, 7, 8, 9, 10, 20, 30, 40, 50, 600, or more repeating units.

The second linker moiety may be the same as or different from the first linker moiety. In some cases, the first linker moiety and the second linker moiety may both be natural polymers. In some cases, the first linker moiety and the second linker moiety may both be synthetic polymers. In some cases, the first linker moiety may comprise at least 1, 2, 3, 4, 5 or more repeating units and the second linker moiety may comprise at least 2, 3, 4, 5, or more repeating units, where the second linker moiety comprises more repeating units than the first linker moiety. In other cases, the first linker may comprise at least 2, 3, 4, 5, or more repeating units and the second linker moiety may comprise 1, 2, 3, 4, 5, or more repeating units, where the first linker moiety comprises more repeating units than the second linker moiety. In such examples, the repeating units of the first linker moiety and the repeating units of the second linker moiety may be the same or different.

In some examples, the second linker moiety may be subjected to a second stimulus. The second linker moiety may be cleaved after being subjected to the second stimulus. In some cases, the second stimulus may be chemical, enzymatic, and/or photochemical.

In some examples, the plurality of nucleotides or nucleotide analogs may further comprise a third subset of nucleotides or nucleotide analogs, wherein none of the third subset of nucleotides or nucleotide analogs comprises a reporter moiety.

In some examples, prior to incorporating the plurality of nucleotides or nucleotide analogs comprising the first subset of nucleotides or nucleotide analogs and the second subset of nucleotides or nucleotide analogs, there may be the addition of an additive. In some cases, the additive may prevent misincorporation. In some cases, the additive may change incorporation rates. In some examples, the additive may be betaine, DMSO, formamide, TMAC, Triton X-100, Tween 20, or Nonidet P-40.

Figure 9:
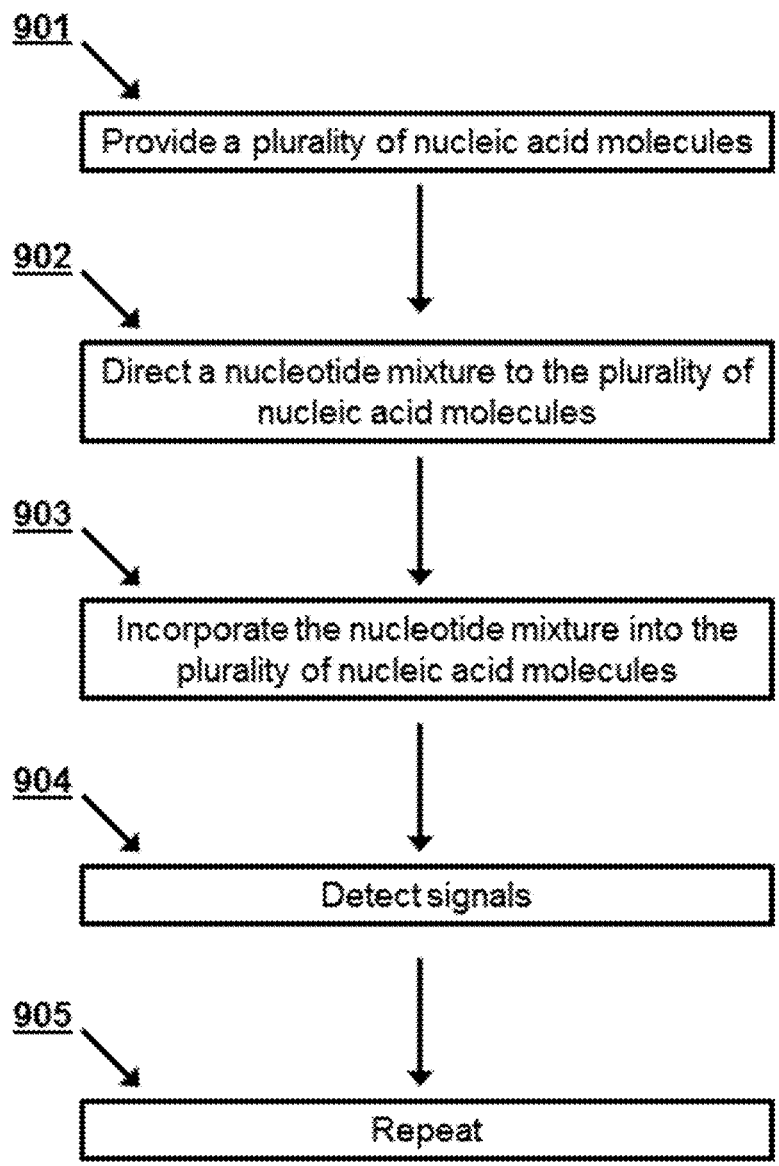
FIG. 9 shows an exemplary workflow for a method of determining a nucleic acid sequence of a target nucleic acid molecule.

FIG. 9 shows an exemplary workflow for a method of determining a nucleic acid sequence of a target nucleic acid molecule. In item 901, a plurality of nucleic acid molecules is provided. The nucleic acid molecules may be immobilized to a support, such as a bead, planar surface, or flow cell. Such a support may be operatively coupled to a detector. In some cases, each of the plurality of nucleic acid molecules exhibits sequence homology to the target nucleic acid molecule. In item 902, a nucleotide mixture is directed to the plurality of nucleic acid molecules. The nucleotide mixture may comprise at least a first subset of nucleotide analogs and a second subset of nucleotide analogs, wherein nucleotide analogs of the first subset and nucleotide analogs of the second subset are different from one another. A given one of the first subset of nucleotide analogs may comprise a reporter moiety and be detectable by said detector (e.g., before, during, and/or after incorporation into a nucleic acid molecule), and a given one of the second subset of nucleotide analogs may not be detectable by said detector (e.g., because it does not yield a detectable signal before, during, and/or after incorporation into a nucleic acid molecule or because the detector is not configured to detect a signal yielded by the nucleotide analog). In item 903, the nucleotide analogs of the nucleotide mixture are incorporated into the plurality of nucleic acid molecules. In item 904, the detector is used to detect a signal associated with the given one of the first subset of nucleotide analogs. In some cases, the detector may also be used to detect a signal associated with the given one of the second subset of nucleotide analogs. In 905, the incorporation and detection processes are repeated one or more times. In some cases, the incorporation and detection processes may be repeated a sufficient number of times to determine all or a portion of the nucleic acid sequence of the target nucleic acid molecule. For example, the incorporation and detection processes may be repeated a sufficient number of times to incorporate and detect a number of nucleotides that is the same as or approximately the same as a number of nucleotides of a nucleic acid sequence of the target nucleic acid molecule.

Systems

In another aspect, the present disclosure provides a system for determining a nucleic acid sequence of a target nucleic acid molecule. The system may comprise a detector. The system may also comprise a support that may be configured to immobilize a plurality of nucleic acid molecules, wherein each of the plurality of nucleic acid molecules may exhibit sequence homology to the target nucleic acid molecule. In this system, the support may be operatively coupled to the detector. Also in this system, the controller may be operatively coupled to the detector. The controller may comprise one or more computer processors. These computer processors may be individually or collectively programmed to direct a plurality of nucleotides or nucleotide analogs to the plurality of nucleic acid molecules immobilized to the support.

In this system, the plurality of nucleotides or nucleotide analogs may comprise at least a first subset of nucleotides or nucleotide analogs and a second subset of nucleotides or nucleotide analogs. A given one of the first subset of nucleotides or nucleotide analogs may comprise a reporter moiety, and a given one of the second subset of nucleotides or nucleotide analogs may comprise another reporter moiety or functional analog thereof. The given one of the first subset of nucleotides or nucleotide analogs may yield a signal that is detectable by the detector. The given one of the second subset of nucleotides or nucleotide analogs may not yield a signal that is detectable by said detector. In some examples, the given one of the second subset of nucleotides or nucleotide analogs may not yield a signal at all. In some examples, a given one of the second subset of nucleotides or nucleotide analogs may have structural homology of at least 50%, 60%, 70%, 80%, 85%, 90%, 95% or more with respect to a given one of the first subset of nucleotides or nucleotide analogs. The term "structural homology" generally refers to the degree of three dimensional shape similarities between nucleotides of the second subset and the first subset.

The system disclosed herein may permit incorporation of the plurality of nucleotides or nucleotide analogs comprising the first subset of nucleotides or nucleotide analogs and the second subset of nucleotides or nucleotide analogs. The incorporation may include the given one of the first subset of nucleotides or nucleotide analogs into the plurality of nucleic acid molecules.

The system disclosed herein may use the detector to detect the signal from the given one of the first subset of nucleotides or nucleotide analogs. By sequentially repeating the incorporation and detection steps, the computer processors may determine the nucleic acid sequence of the target nucleic acid molecule.

Software

In an aspect, there is a non-transitory computer-readable medium that may comprise machine-executable code. Upon execution by one or more computer processors, the machine-executable code may implement a method for determining a nucleic acid sequence of a target nucleic acid molecule. The method being implemented may comprise providing plurality of nucleic acid molecules which may be immobilized to a support (e.g., as described herein). Each of the plurality of nucleic acid molecules may exhibit sequence homology to the target nucleic acid molecule and the support may be operatively coupled to a detector. The method may direct a plurality of nucleotides or nucleotide analogs to the plurality of nucleic acid molecules immobilized to the support. The plurality of nucleotides or nucleotide analogs may comprise at least a first subset of nucleotides or nucleotide analogs and a second subset of nucleotides or nucleotide analogs. A given one of the first subset of nucleotides or nucleotide analogs may comprise a reporter moiety, and a given one of the second subset of nucleotides or nucleotide analogs may comprise another reporter moiety or functional analog thereof. The given one of the first subset of nucleotides or nucleotide analogs may yield a signal that may be detectable by the detector. The given one of the second subset of nucleotides or nucleotide analogs may not yield a signal that is detectable by the detector. The given one of the second subset of nucleotides or nucleotide analogs may not yield a signal at all. In some examples, a given one of the second subset of nucleotides or nucleotide analogs may have structural homology of at least 50%, 60%, 70%, 80%, 85%, 90%, 95% or more with respect to a given one of the first subset of nucleotides or nucleotide analogs. The term "structural homology" generally refers to the degree of three dimensional shape similarities between nucleotides of the second subset and the first subset.

The method may incorporate the plurality of nucleotides or nucleotide analogs comprising the first subset of nucleotides or nucleotide analogs and the second subset of nucleotides or nucleotide analogs. The method may comprise incorporation of the given one of the first subset of nucleotides or nucleotide analogs into the plurality of nucleic acid molecules. The method may the use the detector to detect a signal from the given one of the first subset of nucleotides or nucleotide analogs (e.g., a signal emitted upon excitation or upon incorporation into the plurality of nucleic acid molecules). By sequentially repeating the steps of incorporation and detection, the nucleic acid sequence of the target nucleic acid molecule may be determined.

Computer Control Systems

The present disclosure provides computer control systems that are programmed to implement methods of the disclosure. FIG. 1 shows a computer system 101 that is programmed or otherwise configured to implement methods and systems of the present disclosure, such as performing nucleic acid sequence and sequence analysis.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, results of nucleic acid sequence (e.g., sequence reads, consensus sequences, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105. The algorithm can, for example, implement methods and systems of the present disclosure.

EXAMPLES

Example 1: Molecular Weight within from about 50% or More

In this example, a given one from the first subset of nucleotides or nucleotide analogs and a given one from the second subset of nucleotides or nucleotide analogs are non-natural. The reporter moiety of a given one from the first subset of nucleotides or nucleotide analogs has a molecular weight within 50% of the molecular weight of the reporter moiety of a given one from the second subset of nucleotides or nucleotide analogs.

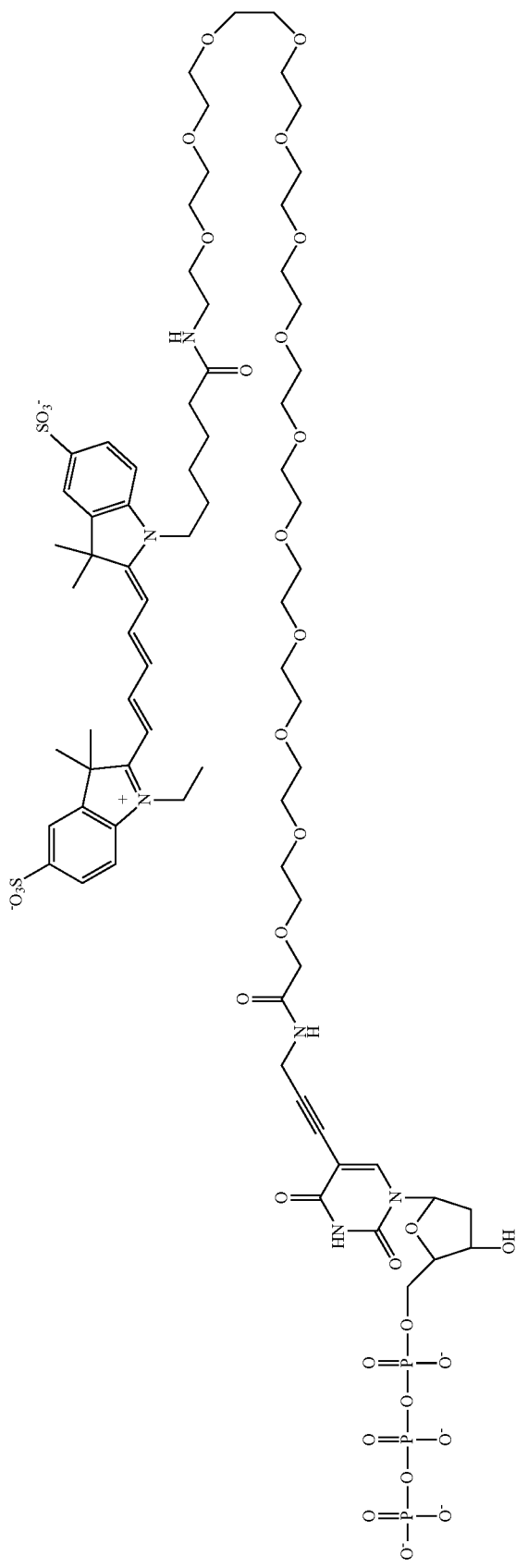
dUTP-PA-PEG12-CY5
R* = PA-PEG12-CY5
MW R* = 1321 g/mol

-continued
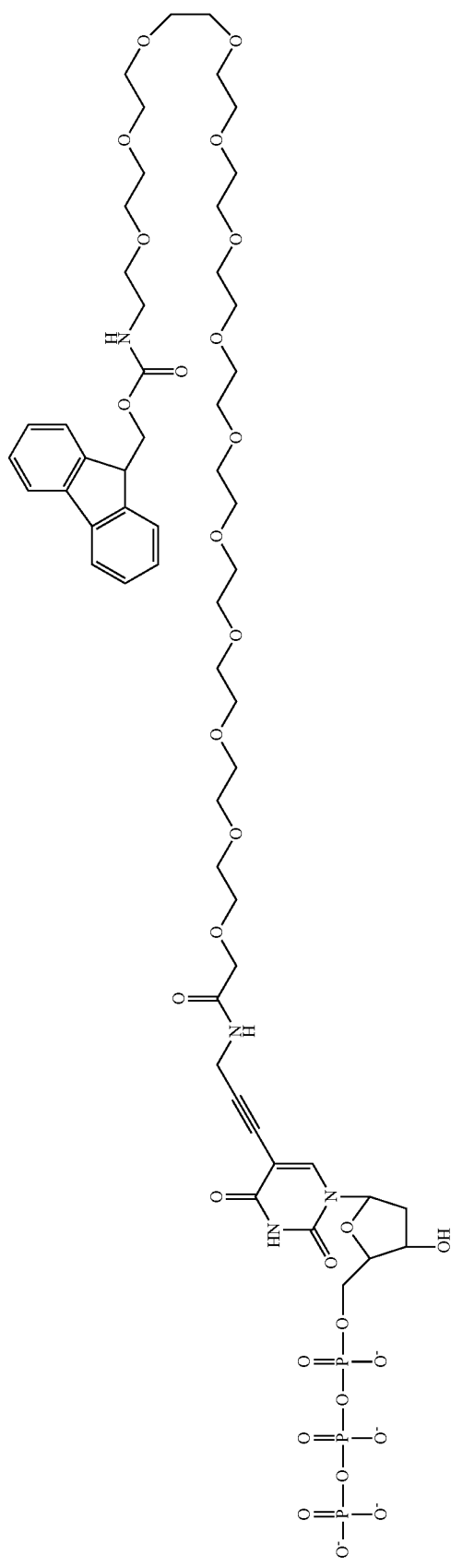
dUTP-PA-PEG12-fmoc
R⁰ = PA-PEG12-fmoc
MW R⁰ = 906 g/mol

The reporter moiety of compound 1 has a molecular weight of 1321 g/mol and the report moiety of compound 2 has a molecular weight of 906 g/mol. The percentage differences in molecular weight between these reporter moieties are 69%. Hence, compound 1 is an example of a given one from the first subset of nucleotides or nucleotide analogs and compound 2 is an example of a given one from the second subset of nucleotides or nucleotide analogs.

Example 2: Tolerance of Reporter Moieties

In this example, a given one from the first subset of nucleotides or nucleotide analogs and a given one from the second subset of nucleotides or nucleotide analogs are non-natural. The ratio of the tolerance by an enzyme of the reporter moiety of a given one from said first subset of nucleotides or nucleotide analogs to the tolerance of the reporter moiety of a given one from said second subset of nucleotides or nucleotide analogs may be greater than the ratio of the tolerance by an enzyme of the reporter moiety of a given one from said first subset of nucleotides or nucleotide analogs to the tolerance of a given one from said third subset of nucleotides or nucleotide analogs. In such an example, the enzyme may prefer to incorporate a given one from the first subset of nucleotides or nucleotide analogs to a given one from the second subset of nucleotides or nucleotide analogs more than it prefers to incorporate a given one from the first subset of nucleotides or nucleotide analogs to a given one from the third subset of nucleotides or nucleotide analogs. Accordingly, the enzyme may discriminate between nucleotides or nucleotide analogs with different features.

An R group comprising a reporter moiety for the second subset of nucleotides or nucleotide analogs may be located in a different area on the molecule than an R group comprising a reporter moiety for the first subset of nucleotides or nucleotide analogs as long as the condition above is met. An R group may be located on a phosphate moiety, sugar moiety, or nucleobase moiety of a nucleotide or nucleotide analog. Some examples of nucleotides or nucleotide analogs having an R group in their phosphate moieties include:

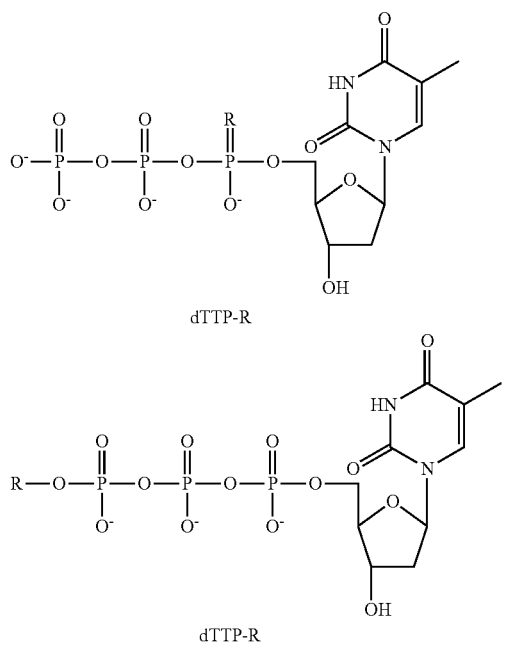

dTTP-R dTTP-R

By way of explanation:

$$S_f^{*/nat} = [dNTP^*]/([dNTP^*]+[dNTP^{nat}]) \quad (1)$$

$$I_f^{*/nat} = dN^*/(dN^*+dN^{nat}) \quad (2)$$

$$T^{*/nat} = I_f^{*/nat}/S_f^{*/nat} \quad (3)$$

$$S_f^{*/0} = [dNTP^*]/([dNTP^*]+[dNTP^0]) \quad (4)$$

$$I_f^{*/0} = dN^*/(dN^*+dN^0) \quad (5)$$

$$T^{*/0} = I_f^{*/0}S_f^{*/0} \quad (6)$$

where

[dNTP*] is the concentration of first subset nucleotides;

[dNTP$^{nat}$] is the concentration of third subset nucleotides;

[dNTP$^0$] is the concentration of second subset nucleotides;

dN* is the incorporated first subset nucleotide;

dN$^{nat}$ is the incorporated third subset nucleotide;

dN$^0$ is the incorporated second subset nucleotide;

$S_f^{*/nat}$ is the solution fraction of first subset nucleotides to the total of first subset nucleotides plus third subset nucleotides;

$I_f^{*/nat}$ is the incorporation fraction of first subset nucleotides to total of first subset plus third subset nucleotides;

$T^{*/nat}$ is the tolerance of enzyme to first subset nucleotides compared to third subset nucleotides;

$Sf^{*/0}$ is the solution fraction of first subset nucleotides to total of first subset plus second subset nucleotides;

$If^{*/0}$ is the incorporation fraction of first subset nucleotides to total of first subset plus second subset nucleotides;

$T^{*/0}$ is the tolerance of enzyme to first subset nucleotides compared to second subset nucleotides;

For example, if there is no discrimination between the reporter nucleotide of a given one of the first subset of nucleotides or nucleotide analogs and a given one of the third subset of nucleotides or nucleotide analogs, then tolerance is about 1. If the enzyme prefers to incorporate a given one of the third subset of nucleotides then tolerance is less than about 1. If the enzyme prefers to incorporate a given one of the first subset of nucleotides or nucleotide analogs, then the tolerance is more than about 1.

Discrimination of an enzyme in favor of one or more different nucleotides or nucleotide analogs of a plurality of nucleotides and/or nucleotide analogs may be useful. For example, discrimination in favor of a nucleotide or nucleotide analog comprising a reporter moiety (e.g., of a first subset of nucleotides or nucleotide analogs as compared to a nucleotide or nucleotide analog of a second or third subset of nucleotides or nucleotide analogs) may facilitate incorporation of a labeled nucleotide or nucleotide analog at a given location in a given template nucleic acid. In other cases, discrimination of an enzyme in favor of one or more different nucleotides or nucleotide analogs may indicate that the enzyme incorporates nucleotides and/or nucleotide analogs in a context-dependent manner.

Example 3: Non-Natural Nucleotide Pair A

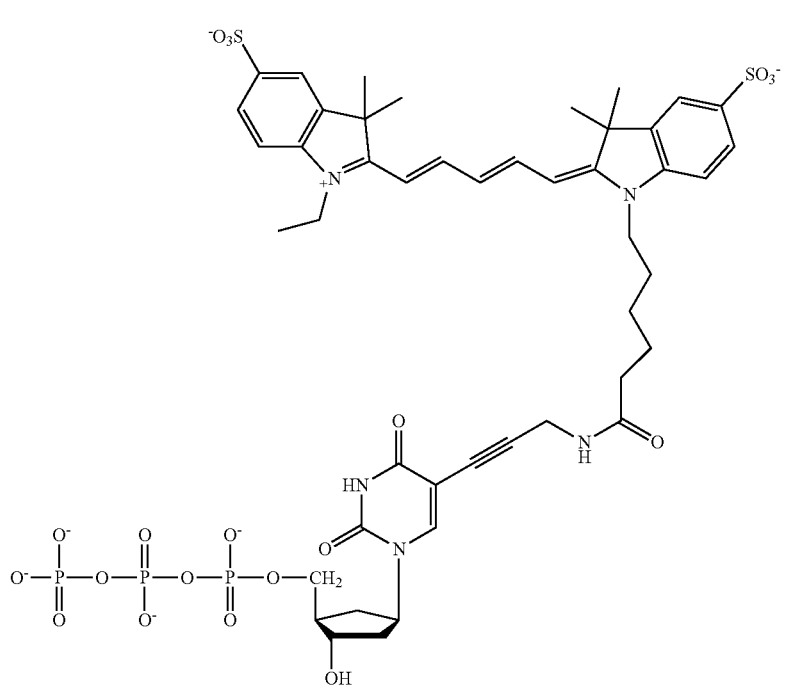

3

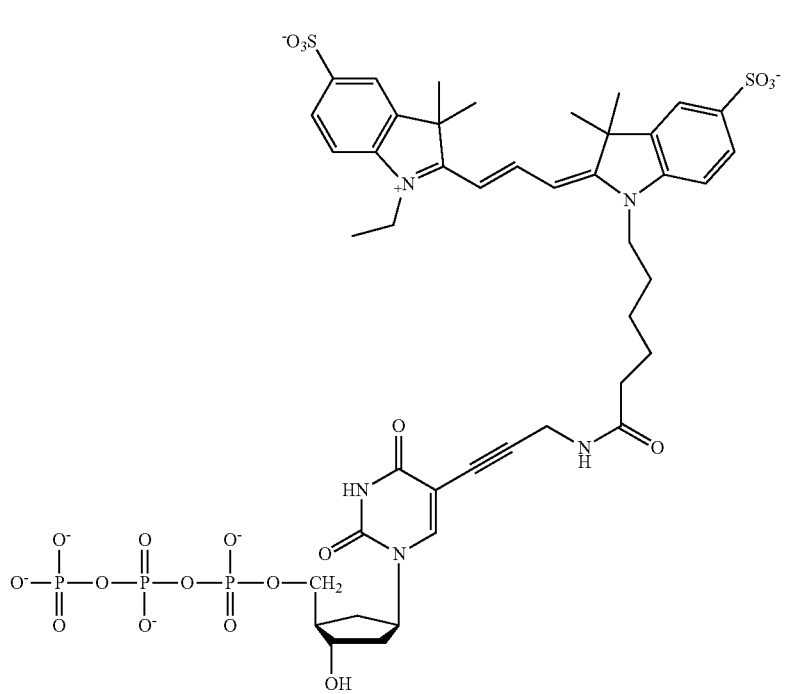

4

The non-natural nucleotides 3 and 4 differ only by two carbon atoms. Although both include fluorescent dye moieties, the dye moiety of 3 functions as a reporter which yields a signal that is detectable by the detector and the dye moiety of 4 functions as a reporter that does not yield a signal detectable by the detector. This is because only 3 remains unquenched when both 3 and 4 are incorporated within a few bases on the same oligonucleotide strand.

Example 4: Non-Natural Nucleotide Pair B

Example 5: Non-Natural Nucleotide Pair C

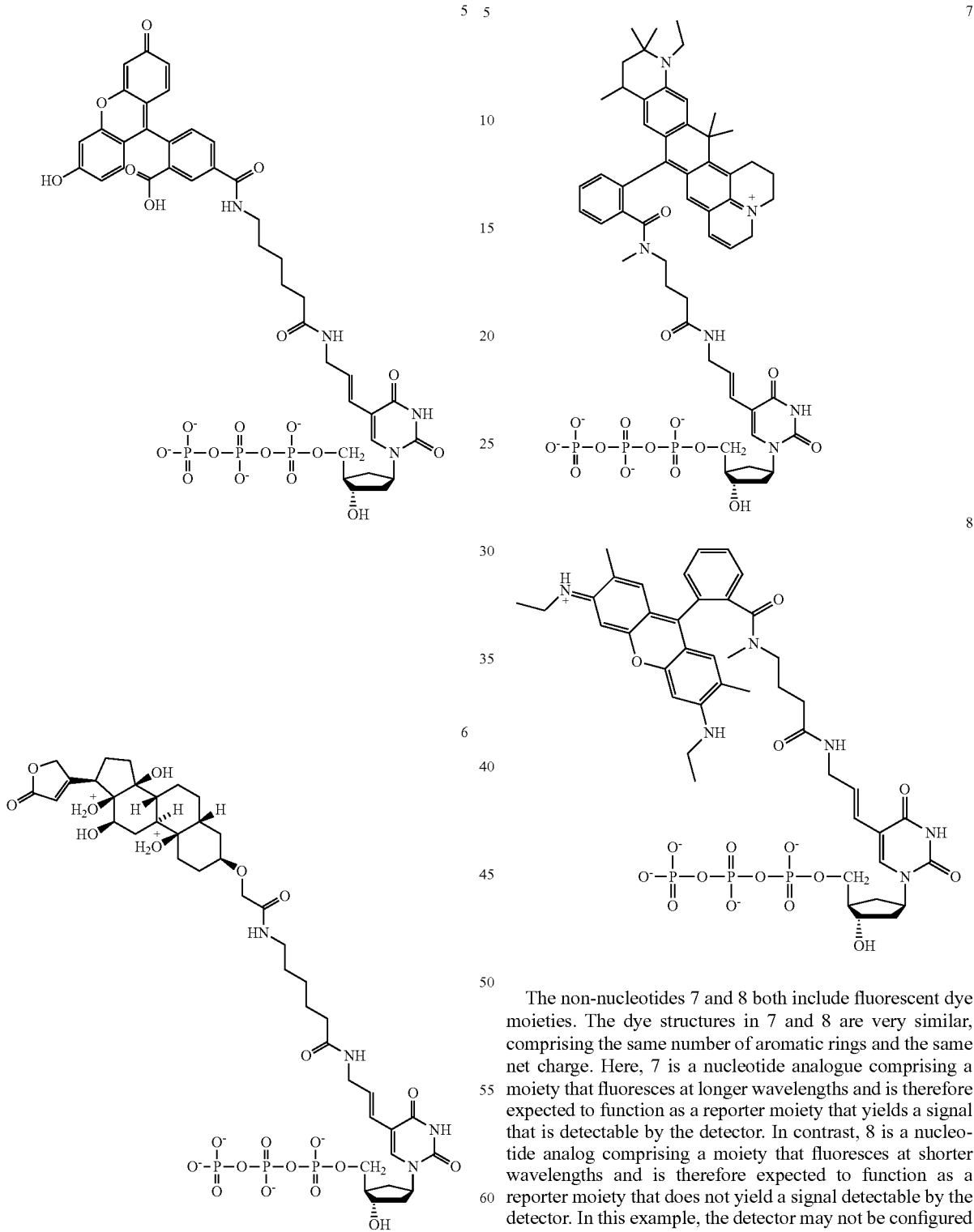

The non-natural nucleotides 5 and 6 are examples of a fluorescent nucleotide and a non-fluorescent nucleotide, respectively. Here, 5 includes a moiety that is approximately the same size and steric bulk as the reporter moiety on 6.

The non-nucleotides 7 and 8 both include fluorescent dye moieties. The dye structures in 7 and 8 are very similar, comprising the same number of aromatic rings and the same net charge. Here, 7 is a nucleotide analogue comprising a moiety that fluoresces at longer wavelengths and is therefore expected to function as a reporter moiety that yields a signal that is detectable by the detector. In contrast, 8 is a nucleotide analog comprising a moiety that fluoresces at shorter wavelengths and is therefore expected to function as a reporter moiety that does not yield a signal detectable by the detector. In this example, the detector may not be configured to detect such shorter wavelengths due to, for instance, the use of a filter or other wavelength selection mechanism and/or a sensitivity of the detector. Alternatively, the detector may be configured to detect a signal corresponding to such shorter wavelengths but may be capable of distinguishing between different wavelengths. For example, the detector may collect different signals corresponding to different fluorescent dye moieties at different times, at different locations, and/or with different sensitivities.

Example 6: Competition Assay

An example competition assay was performed to evaluate the incorporation accuracy and efficiency of a dUTP-Cy-3 nucleotide analogue when competing with a dUTP-Cy-5 and also a naturally occurring nucleotide dTTP nucleotide. Four different reaction mixtures were tested: (i) dUTP-Cy-3 only ("dUTP*"), (ii) dUTP-Cy-5 only ("dUTP$^O$"), (iii) dTTP only, and (iv) 1:1 dUTP*:dUTP$^O$. The final concentrations of various nucleotides in the mixtures were 5 micromolar (μM). The structures of dUTP* and dUTP$^O$ are given by 9 and 10, respectively, below.

A solution of biotinylated template (2 microliters (μL) of 100 μM) and dye-labeled primer (4 μL of 100 μM) were combined in annealing buffer (40 μL; Tris (10 millimolar (mM)), EDTA (1 mM), NaCl (100 mM)). The resulting solution was heated to 95° C. and allowed to slowly cool to room temperature. A portion of this solution (8 μL) was mixed with streptavidin-labeled magnetic beads (4 μL of Invitrogen Dynabeads™ MyOne™ Streptavidin C1, 10 milligrams/milliliter (mg/mL); washed and eluant removed) and 2× bead wash buffer (8 μL; 10 mM Tris, pH 7.5, 1 mM EDTA, 2 M NaCl, 0.01% Triton X-100). After washing with TET solution (10 mM Tris, 1 mM EDTA, 0.05% Triton X-100) the beads were treated with Bst DNA polymerase v.2.0 (8 μL of 8 units (U)/μL; New England Biolabs) for five minutes. The excess enzyme was removed by washing with TET and the beads were suspended in 1×DNA polymerase

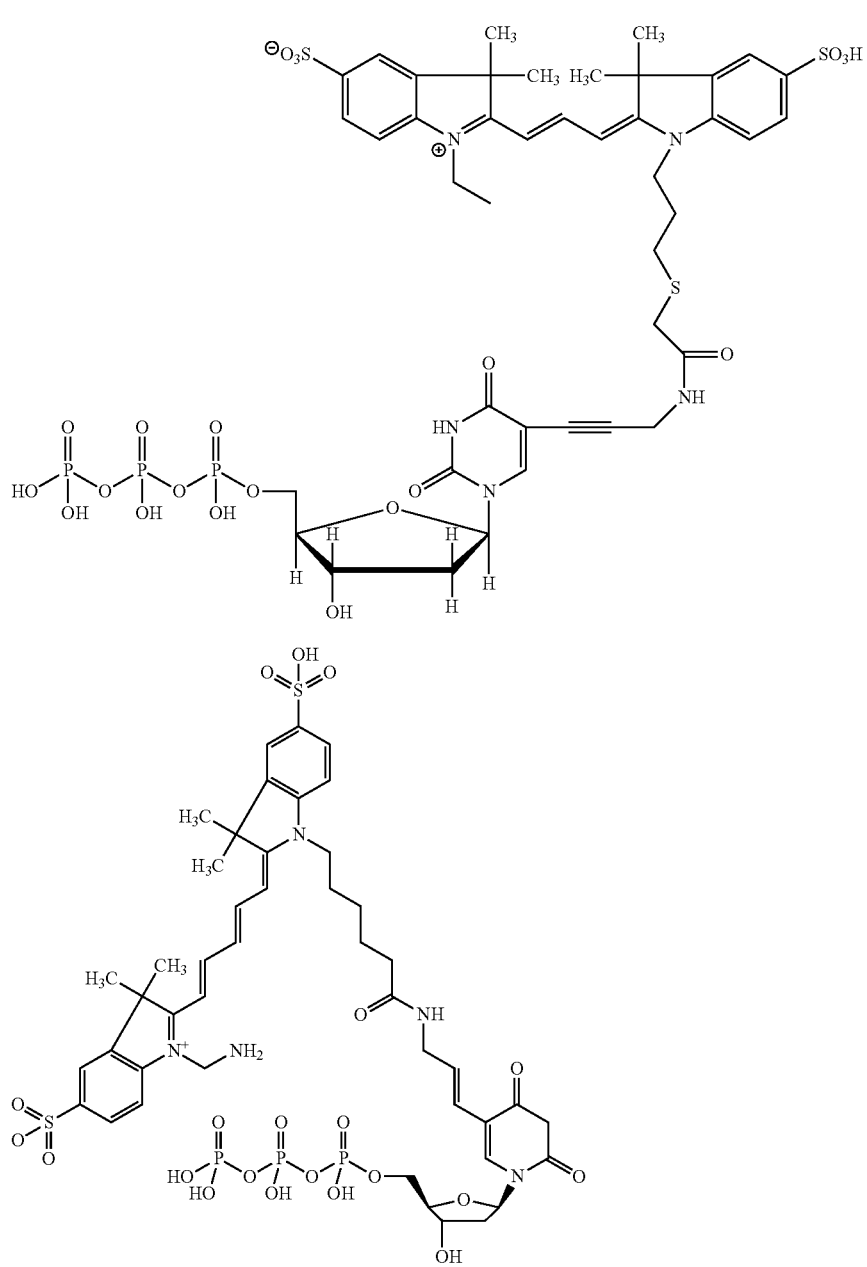

buffer solution (20 mM Tris, pH 8, 10 mM NaCl, 2 mM MgCl$_2$, 0.01% Triton X-100). The sequence of the biotinylated template was /52 Bio//iSp18/ TTGCTTGCTTGCTTGCACTGAGTCGGAGACACG CAGGGATGAGATGG (SEQ ID NO: 12), where "5" is indicative of the 5'-end of the oligo, 2-Bio indicates dual biotin, and iSP18 indicates a PEG spacer. The underlined portion shows the region hybridized by the dye-labeled primer. The sequence of dye-labeled primer was 5-JOE CCATCTCATCCCTGCGTG TCTCCGACTCAG (SEQ ID NO: 13), where "5" indicates the 5'-end of the oligo and JOE indicates a fluorescent dye attached to the oligo.

Figure 2:
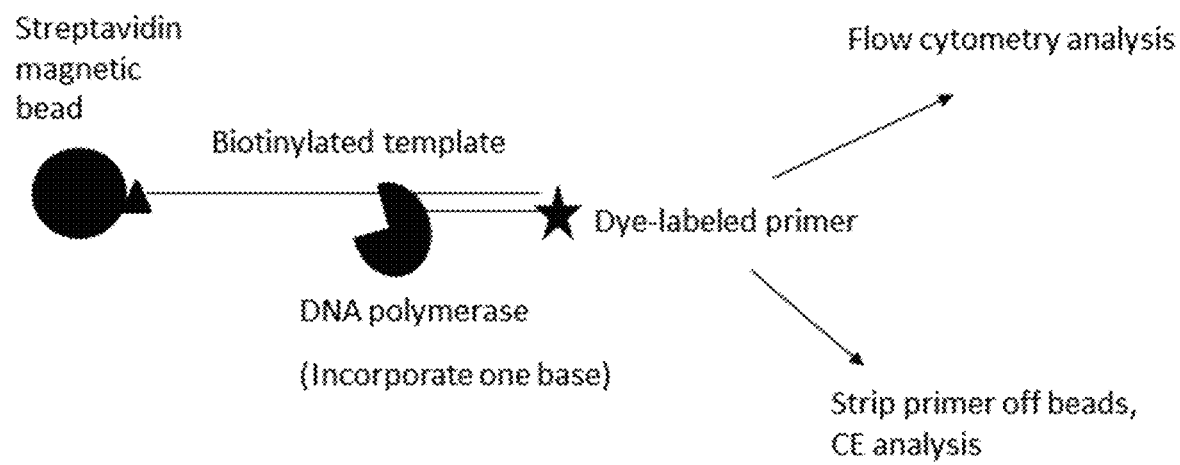
FIG. 2 schematically summarizes experiments of Example 6.

Next, a portion of the suspended magnetic beads (10 µL) were removed and placed in a PCR tube. A solution of nucleotides (10 µL) was added to the tube and the tube incubated for 40 seconds (s) at 50° C. The enzyme reaction was stopped with the addition of 5 µL of 50 mM EDTA. The beads were washed with 2×100 µL TET and resuspended in 20 µL TET. A portion of the bead solution (1 µL) was added to TE (200 µL) and the beads examined for red fluorescence on a flow cytometer (BD Accuri™, APC channel). The eluant of the remaining beads was removed and 40 µL of 95:5 formamide:10 mM EDTA was added to the beads. A portion of the formamide solution (1 µL) was added to 40 µL 95:5 formamide EDTA. The solutions were examined by capillary electrophoresis (CE) on an ABI 3730 instrument and the peaks identified and quantitated by peak height. The experimental protocol is summarized schematically in FIG. 2.

Figure 3:
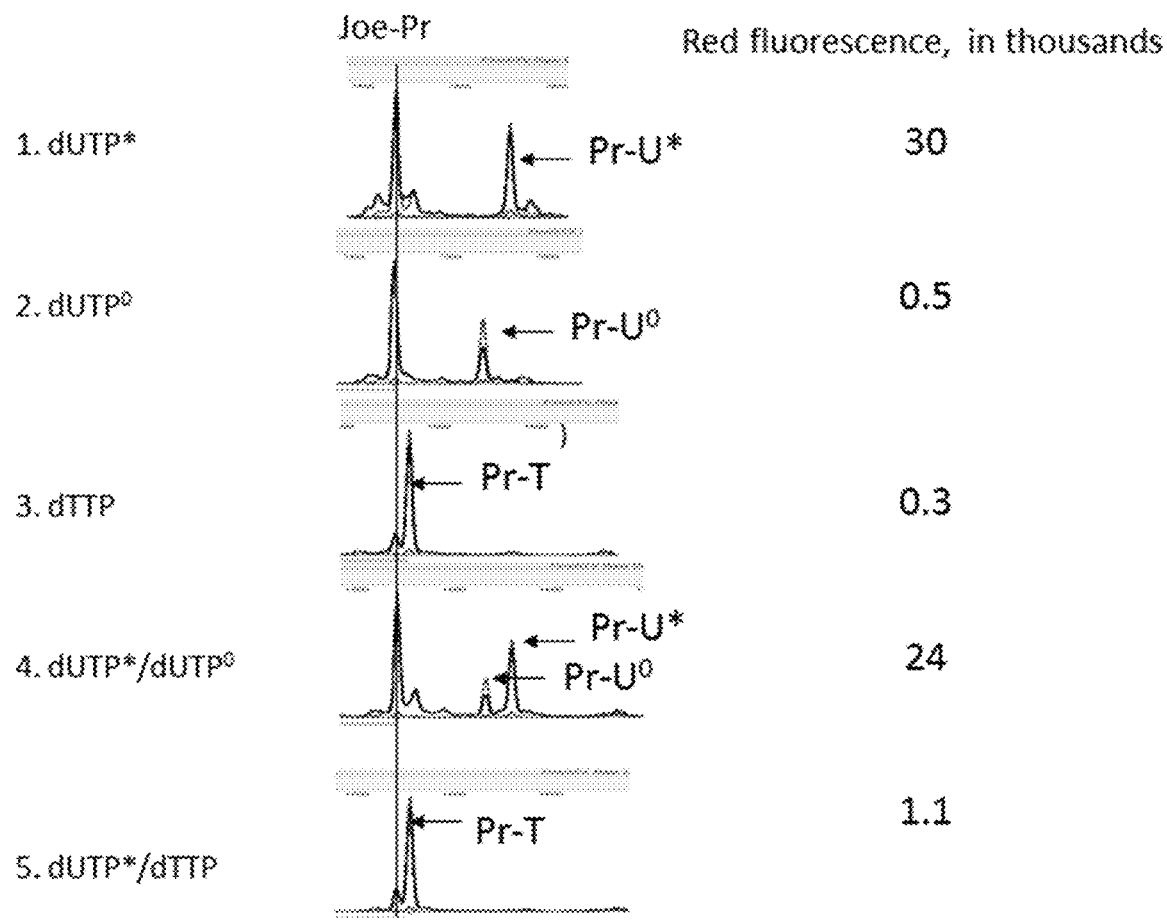
FIG. 3A graphically summarizes the results of capillary electrophoresis (CE) experiments in Example 6.
FIG. 3B tabulates the results of flow cytometry experiments in Example 6.

The results of one base extension from CE analysis are graphically depicted in FIG. 3A. As shown in FIG. 3A, products peaks are identified where Pr-U* corresponds to incorporation of a dUTP* nucleotide, Pr-U$^0$ corresponds to incorporation of a dUTP$^0$ nucleotide, and Pr-T corresponds to incorporation of a dTTP nucleotide. CE results show the residual primer peaks (Joe-Pr) aligned with the thin vertical line. As shown, competition of dUTP* and dUTP$^0$ yields a Pr-U* peak and a Pr-U$^0$ peak, while competition of dUTP* and dTTP yields only a Pr-T peak, suggesting that little, if any, dUTP* is incorporated. Unexpectedly, a rate of incorporation of an unnatural nucleotide may be greater than a rate of incorporation of a natural nucleotide.

The corresponding results of one base extension from flow cytometry are numerically tabulated in FIG. 3B. Data correspond to beads before stripping. The results in FIG. 3B also suggest that competition between dUTP* and dUTP$^0$ yields dUTP* incorporation, whereas signals from dUTP* and dTTP competition are relatively low.

A summary of data from FIGS. 3A-3B, including yield percentages, is tabulated in FIG. 4.

Example 7: Tolerance of dUTP Analogs

11

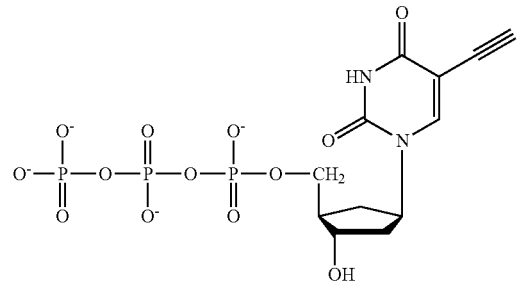

12

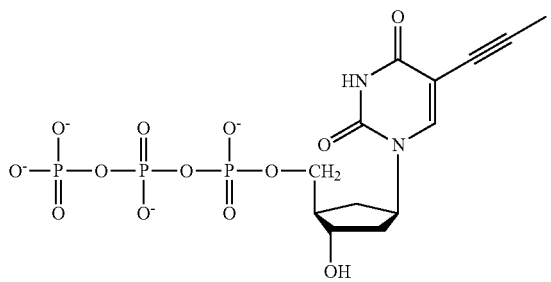

13

14

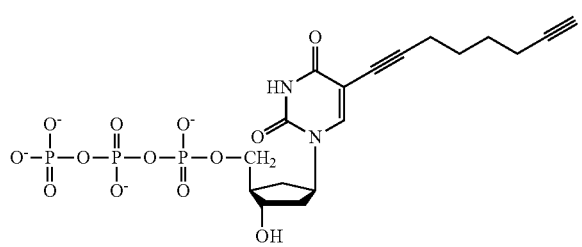

Nucleotide analogs 11 (TTP), 12 (ethynyl-dUTP or E-dUTP), 13 (propynyl-dUTP or P-dUTP), and 14 (di-octynyl-dUTP or O-dUTP) are analogs of dUTP. TTP is a natural occurring nucleotide and serves as a useful control, while E-dUTP, P-dUTP, and O-dUTP are non-naturally occurring nucleotide analogs.

Flow Cytometry Assay:

To determine the tolerance of dye-labeled nucleotide dUTP* compared to each nucleotide analog dUTP$^0$ (e.g., TTP, E-dUTP, P-dUTP, and O-dUTP), a flow cytometry assay was performed, as described in Example 6 above. Briefly, a primer was annealed to a biotinylated template on streptavidin-linked magnetic beads. dUTP* and/or dUTP$^0$ and DNA polymerase were combined with the beads and subjected to appropriate reaction conditions. Excess nucleotides and nucleotide analogs were washed away and the sample was diluted and measured using a flow cytometer. Tolerance was measured at two molar fractions, 05 and 0.05, for each of the four dUTP analogs. Results are summarized in Table 1 below:

TABLE 1

Flow cytometry results using dUTP analogs

| dUTP$^0$ | Molar fraction dUTP* | Red signal | Apparent fraction | Tolerance |
|---|---|---|---|---|
| None | 1 | 50,000 | | |
| TTP | 0.5 | 21,000 | 0.42 | 0.8 |

TABLE 1-continued

Flow cytometry results using dUTP analogs

| dUTP⁰ | Molar fraction dUTP* | Red signal | Apparent fraction | Tolerance |
|---|---|---|---|---|
| TTP | 0.05 | 2,900 | 0.058 | 1.2 |
| P-dUTP | 0.5 | 16,000 | 0.32 | 0.6 |
| P-dUTP | 0.05 | 1,600 | 0.032 | 0.6 |
| O-dUTP | 0.5 | 35,000 | 0.7 | 1.4 |
| O-dUTP | 0.05 | 12,000 | 0.24 | 5 |
| E-dUTP | 0.5 | 23,000 | 0.46 | 0.9 |
| E-dUTP | 0.05 | 2,200 | 0.044 | 0.9 |

As shown in Table 1, the tolerance of dUTP* with E-DUTP most closely matches TTP. The tolerance is close to 1 in all cases. P-dUTP outperforms TTP as a substrate, as evidenced by a lower tolerance for the labeled nucleotide at both molar fractions, and O-dUTP is a worse substrate than TTP, as evidenced by a higher tolerance for the labeled nucleotide at both molar fractions.

Figure 5A:
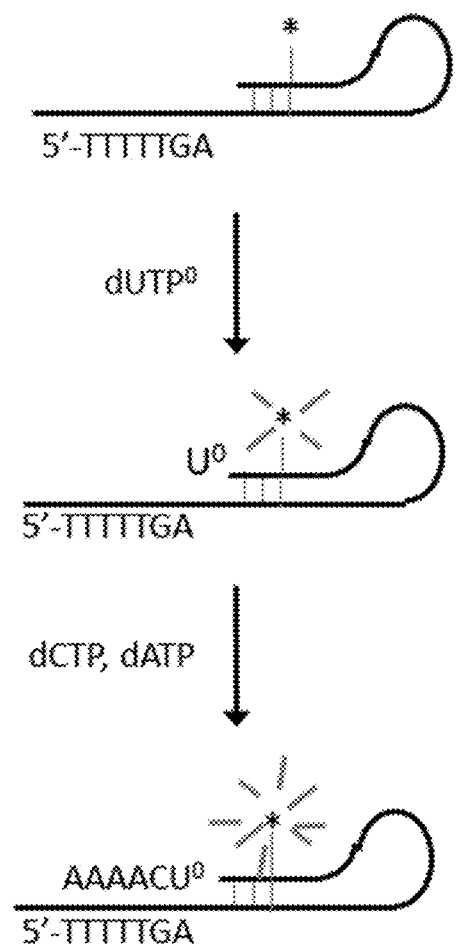
FIG. 5A shows the scheme for the kinetic assay of Example 7.

Kinetic Assay:

A kinetic assay using hairpin oligos was also performed to determine the rate of incorporate of an unnatural nucleotide and a natural nucleotide following the unnatural nucleotide. FIG. 5A shows the scheme for this kinetic assay. Incorporation of a T or U analog unquenched a fluorescein in the hairpin oligo. Following incorporation of the T or U analog, a mixture of C and A was added, which further unquenched the dye. The sequence of the hairpin oligo was 5'-TTT TTG AGG AGG TGA CAG GTT TTT CCT GTC ACC T*-CC (SEQ ID NO: 14), where the "*" indicates that the nucleotide bears a fluorescein moiety.

Figure 5B:
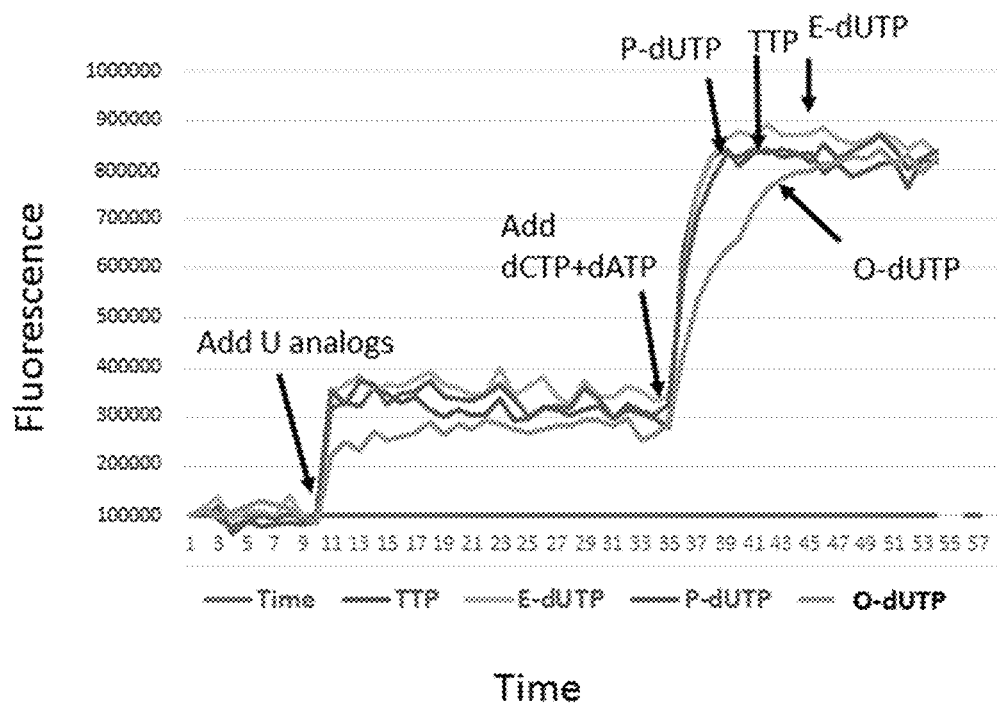
FIG. 5B graphically summarizes the results of the kinetic assay of Example 7.

As shown in FIG. 5B, initial incorporation of dUTP analogs TTP, E-dUTP, P-dUTP, and O-dUTP was rapid. Incorporation of dCTP and dATP after the dUTP analogs was rapid, except for incorporation of dCTP and dATP after O-dUTP. The slowing of subsequent incorporations suggested that O-dUTP is not an optimal unnatural nucleotide.

Figure 6A:
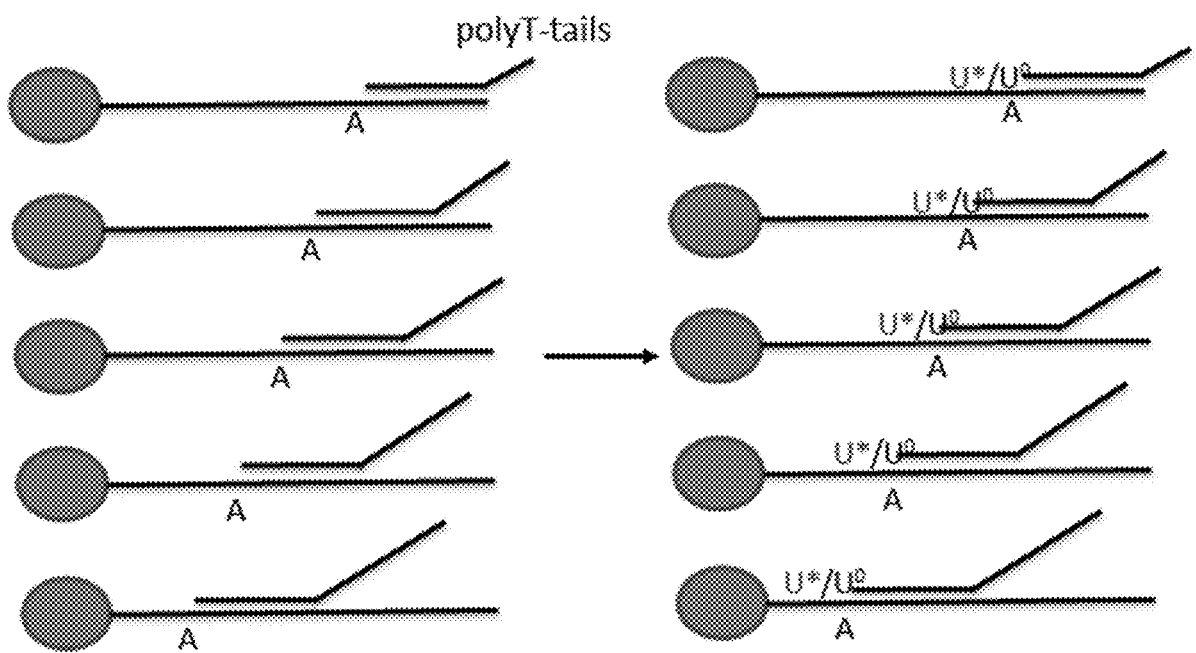
FIG. 6A shows the scheme for gel assay of Example 7.
Figure 6B:
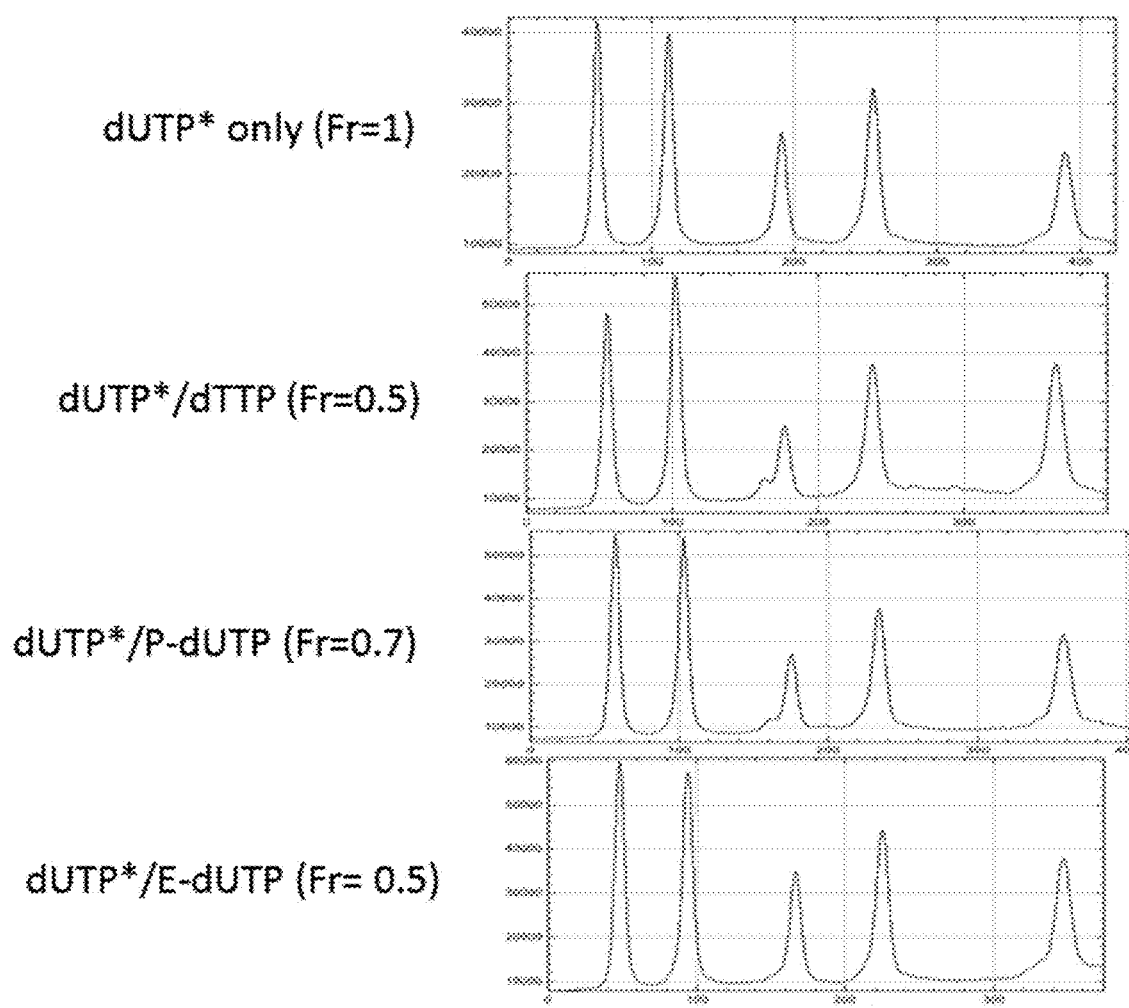
FIG. 6B graphically summarizes the results of capillary electrophoresis (CE) experiments in Example 7.

Gel Assay:

A gel assay was also performed to examine context-dependent incorporation. Five different primers with different contexts at their 3' ends were extended with dUTP* alone (fraction=1) and with different ratios of dUTP*:dUTP⁰. The different ratios of dUTP*:dUTP⁰ were intended to give approximately a ratio of 1:1 labeled to unlabeled. The primers had different lengths poly-T tails to enable separation on a polyacrylamide gel. The composition of dUTP⁰ for this experiment included TTP, E-dUTP, and P-dUTP. FIG. 6A shows the scheme for this assay. Briefly, a primer was annealed to a biotinylated template on streptavidin-linked magnetic beads. dUTP* and/or dUTP⁰ and DNA polymerase were combined with the beads and subjected to appropriate reaction conditions. Excess nucleotides and nucleotide analogs were washed away and the sample was loaded onto a gel. FIG. 6B shows the CE signal corresponding to each condition studied, while Table 2 below summarizes the results:

| Peak | dUTP* only (Fr = 1.0) | dUTP*/ dTTP | Norm. | dUTP*/ P-dUTP | Norm. | dU*/ E-dUTP | Norm. |
|---|---|---|---|---|---|---|---|
| 1 | 42 | 48 | 1.1 | 55 | 1.3 | 59 | 1.4 |
| 2 | 40 | 56 | 1.4 | 54 | 1.4 | 56 | 1.4 |
| 3 | 26 | 25 | 1.0 | 27 | 1.0 | 33 | 1.3 |
| 4 | 32 | 38 | 1.2 | 36 | 1.1 | 43 | 1.3 |
| 5 | 23 | 38 | 1.7 | 32 | 1.4 | 38 | 1.7 |

The red fluorescence on the gel was analyzed with ImageJ. The peak heights for the extension reactions for each primer with Fr=1.0 was measured. The peak heights for dUTP*/dUTP⁰ were also measured and compared to Fr=1.0. The ratios of the peak heights for each pair were calculated ("norm."). As shown in FIG. 6B and Table 2, the set of pairs with the least variation in the norm was the extension with dUTP*/E-dUTP. The metric in this experiment was context, as defined as: C=(Maximum signal–minimum signal)/(average signal). Zero context-dependent incorporation would provide a C value of 0. The contexts for TTP, P-dUTP, and E-dUTP were 0.54, 0.32, and 0.28, respectively.

Example 8: Stepwise Sequencing with TTP and E-dUTP

A microscope slide surface was modified with polyaminosilane to allow the attachment of 1 micron beads each containing one of three different oligonucleotide templates. To each template was bound an oligonucleotide primer and Bst DNA polymerase. Solutions of mixtures of labeled and unlabeled nucleotide, of one type at a time, were exposed to the surface, followed by a wash solution. The fluorescence of labeled beads was detected and quantitated. The fluorescence label was cleaved by treatment with tris(hydroxypropyl)phosphine (THP) after each step.

A control experiment for each template performed sequencing with a 0.05 fraction of dNTP*/dNTP, where all the dNTPs are natural nucleotides (the concentrations used to achieve a 0.05 fraction are 0.05 uM dUTP* and 0.95 uM dUTP⁰, where dUTP⁰=E-dUTP or TTP.) The test experiment shows compared the results of substituting TTP with E-dUTP, with an 0.05 fraction of dUTP*. Context was measured for each experiment. Context is given by the context metric, C, which is defined as the (maximum-minimum signal)/average signal. Results are summarized in Table 3 below:

TABLE 3

Replacement of TTP with E-dUTP

| Oligonucleotide template | Nucleotide | C |
|---|---|---|
| 1 | TTP | 0.86 |
|   | E-dUTP | 0.39 |
| 2 | TTP | 0.73 |
|   | E-dUTP | 0.59 |
| 3 | TTP | 0.71 |
|   | E-dUTP | 0.27 |

As summarized in Table 3, the experiment shows an improvement in the value of C when E-dUTP is used in place of TTP for each of three different oligonucleotide templates. Further, the use of E-dUTP does not appear to negatively impact the context metric for other bases. Surprisingly, a rate of incorporation of an unnatural nucleotide may be greater than a rate of incorporation of a natural nucleotide. A faster rate of incorporation can lead to more rapid stepwise cycle times, and thus shorten the overall sequencing time.

Example 9: Tolerance of dCTP Analogs

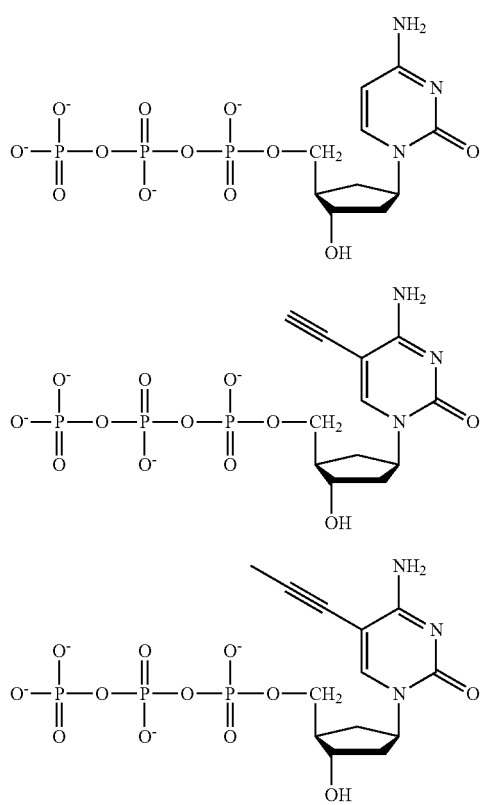

Nucleotide analogs 16 (ethynyl-dCTP or E-dCTP) and 17 (propynyl-dUTP or P-dUTP) or naturally occurring nucleotide 15 (dCTP) are shown.

A homopolymer assay was performed to investigate the effectiveness of E-dCTP and P-dUTP as nucleotide analogs of dCTP. 50 µl solutions containing a template nucleic acid molecule and primer and Bst 2.0 DNA polymerase are placed in a microplate reader and the fluorescence of the solution is measured in kinetic mode. A fluorescein attached to an oligonucleotide (indicated with a * in FIG. 7) was quenched in the substrate due to the proximity of complementary G bases. Addition of dCTP and/or dCTP analogs causes extension of the 3′ end of the primer, formation of double-stranded DNA, and unquenching of the fluorescein. The fluorescence increases with the addition of multiple nucleotides.

FIG. 7 shows the rates of fluorescence for dCTP, E-dCTP, and P-dCTP. The rates of incorporation of both P-dCTP and E-dCTP are much faster than that of natural dCTP. This unexpectedly indicates that an unnatural nucleotide may be incorporated more rapidly than a natural nucleotide.

Example 10: Homopolymer Assays

Additional homopolymer assays were performed according to the procedure outlined in Example 8 using different nucleotides and nucleotide analogs. The oligonucleotide sequences used in homopolymer sequences are provided in Table 4 below:

TABLE 4

Sequences of oligonucleotides and primers used in homopolymer assays

| Oligo/Primer | Sequence |
|---|---|
| 332 | 5′-AAAAAAAGGAGGTGACAGGTTGGAGAAACCGT (SEQ ID NO: 4) |
| 333 | 5′-GGGGGGGGAGGTGACAGGTTGGAGAAACCGT (SEQ ID NO: 15) |
| 334 | 5′-CCCCCCCGGAGGTGACAGGTTGGAGAAACCGT (SEQ ID NO: 6) |
| 221L | 5′-ACGGTTTCTCCAACCTGTCACC/iFluorT/CC (SEQ ID NO: 3) |
| 221 | 5′-TTTTTTTGGAGGTGACAGGTTTTTCCTGTCACC/ iFluorT/CC (SEQ ID NO: 7) |

To test for dUTP or TTP incorporation, oligo 332 was used as a template and oligo 221L was used as a primer. To test for dCTP incorporation, oligo 333 was used as a template and oligo 221L was used as a primer. To test for dGTP incorporation, oligo 334 was used as a template and oligo 221L was used as a primer. To test for dATP incorporation, hairpin oligo 221 was used as both a primer and template.

Figure 8:
FIG. 8 shows the sequences used in the homopolymer assays of Example 10.

FIG. 8 shows the oligonucleotide sequences used for homopolymer assays. The nucleotide analogs used in homopolymer assays, as well as their performance therein, are summarized in Table 5 below:

TABLE 5

Nucleotide analogs used in homopolymer assays

| Natural Nucleotide | Nucleotide Analog | Relative Rate in Homopolymer Assay |
|---|---|---|
| T | TTP | 1 |
|  | 5-Propynyl-dUTP | >1 |
|  | 5-Bromo-dUTP | >1 |
|  | 5-Iodo-dUTP | >1 |
|  | 5-Ethynyl-dUTP | <1 |
|  | 5-Fluoro-dUTP | <1 |
|  | 5-Propargylamino-dUTP | <<1 |
|  | 5-C8-alkyne-dUTP | <<1 |
| C | dCTP | 1 |
|  | 5-Methyl-dCTP | >1 |
|  | 5-Bromo-dCTP | >1 |
|  | 5-Propynyl-dCTP | >1 |
|  | 5-Ethynyl-dCTP | >1 |
|  | 5-Hydroxy-dCTP | <<1 |
|  | 5-Hydroxymethyl-dCTP | <<1 |
|  | 5-formyl-dCTP | <<1 |
| A | dATP | 1 |
|  | Bromo-dATP | >1 |
|  | 7-Iodo-7-deaza-dATP | >1 |
|  | 7-deaza-dATP | <1 |
| G | dGTP | 1 |
|  | Iodo-dGTP | >1 |
|  | 7-deaza-dGTP | <1 |

Experiments were performed replacing dCTP with P-dCTP for three different oligonucleotide templates. Table 6 summarizes the context metrics associated with each test.

TABLE 6

| Oligonucleotide template | Nucleotide | C |
|---|---|---|
| 1 | dCTP | 0.85 |
|   | P-dCTP | 0.31 |
| 2 | dCTP | 0.72 |
|   | P-dCTP | 0.31 |
| 3 | dCTP | 0.70 |
|   | P-dCTP | 0.41 |

Replacement of dCTP with P-dCTP

As summarized in Table 6, the experiment shows an improvement in the value of C when P-dCTP is used in place of dCTP for each of three different oligonucleotide templates.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for determining a nucleic acid sequence of a target nucleic acid molecule, comprising:
   (a) providing a plurality of nucleic acid molecules immobilized to a support, wherein each of said plurality of nucleic acid molecules exhibits sequence homology to said target nucleic acid molecule, and wherein said support is in optical communication with a detector;
   (b) directing a nucleotide mixture to said plurality of nucleic acid molecules immobilized to said support, which said nucleotide mixture comprises at least a first subset of nucleotide analogs and a second subset of nucleotide analogs of a same canonical base type, wherein nucleotide analogs of said first subset and said second subset are different from one another, wherein a given one of said first subset of nucleotide analogs comprises a reporter moiety and is detectable by said detector, wherein a given one of said second subset of nucleotide analogs comprises an analog of said reporter moiety, and wherein said given one of said second subset of nucleotide analogs does not yield a signal that is detectable by said detector;
   (c) incorporating said nucleotide mixture comprising at least said first subset of nucleotide analogs and said second subset of nucleotide analogs into growing nucleic acid strands hybridized to said plurality of nucleic acid molecules;
   (d) using said detector to detect signals indicative of a presence, or lack thereof, of said given one of said first subset of nucleotide analogs and not of said given one of said second subset of nucleotide analogs; and
   (e) repeating (c) and (d), thereby determining said nucleic acid sequence of said target nucleic acid molecule.

2. The method of claim 1, wherein said nucleotide mixture further comprises naturally occurring nucleotides.

3. The method of claim 1, wherein said reporter moiety comprises a fluorophore.

4. The method of claim 1, wherein during incorporation, said given one of said first subset of nucleotide analogs and said given one of said second subset of nucleotide analogs are indistinguishable by an enzyme facilitating said incorporation, wherein said enzyme is used to incorporate both said first subset of nucleotide analogs and said second subset of nucleotide analogs.

5. The method of claim 1, wherein said first subset of nucleotide analogs or said second subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

6. The method of claim 1, wherein said nucleotide mixture further comprises a third subset of nucleotides or nucleotide analogs, wherein none of said third subset of nucleotides or nucleotide analogs comprises a reporter moiety.

7. The method of claim 1, wherein prior to (c), an additive is added, wherein said additive prevents misincorporation or changes incorporation rates.

8. The method of claim 1 wherein said reporter moiety of said given one of said first subset of nucleotide analogs has a molecular weight within 50% of a molecular weight of said analog of said reporter moiety of said given one of said second subset of nucleotide analogs.

9. The method of claim 1, wherein a first Michaelis constant ($K_m$) of a polymerase reaction with said first subset of nucleotide analogs and a second $K_m$ for a polymerase reaction with said second subset of nucleotide analogs are within 30% of one another using a same enzyme.

10. The method of claim 1, wherein said reporter moiety of said given one of said first subset of nucleotide analogs and said analog of said reporter moiety of said given one of said second subset of nucleotide analogs are different by 2 carbon atoms.

11. The method of claim 1, wherein said analog of said reporter moiety of said given one of said second subset of nucleotide analogs comprises a dye moiety.

12. A method for determining a nucleic acid sequence of a target nucleic acid molecule, comprising:
   (a) providing a plurality of nucleic acid molecules immobilized to a support, wherein each of said plurality of nucleic acid molecules exhibits sequence homology to said target nucleic acid molecule, and wherein said support is in optical communication with a detector;
   (b) directing a nucleotide mixture to said plurality of nucleic acid molecules immobilized to said support, which said nucleotide mixture comprises at least a first subset of nucleotide analogs and a second subset of nucleotide analogs of a same canonical base type, wherein (i) a given one of said first subset of nucleotide analogs comprises a reporter moiety, (ii) a given one of said second subset of nucleotide analogs comprises an analog of said reporter moiety, (iii) said given one of said first subset of nucleotide analogs yields a signal that is detectable by said detector, (iv) said given one of said second subset of nucleotide analogs does not yield a signal that is detectable by said detector, (v) said given one of said second subset of nucleotide analogs has structural homology of 85% or more with respect to said given one of said first subset of nucleotide analogs;
   (c) incorporating said nucleotide mixture comprising at least said first subset of nucleotide analogs and said second subset of nucleotide analogs, including said given one of said first subset of nucleotide analogs, into growing nucleic acid strands hybridized to said plurality of nucleic acid molecules;
   (d) using said detector to detect said signal indicative of a presence, or lack thereof, of said given one of said first subset of nucleotide analogs and not of said given one of said second subset of nucleotide analogs; and
   (e) repeating (c) and (d), thereby determining said nucleic acid sequence of said target nucleic acid molecule.

13. The method of claim 12, wherein said nucleotide mixture further comprises naturally occurring nucleotides.

14. The method of claim 12, wherein said analog of said reporter moiety comprises a quencher.

15. The method of claim 12, wherein said given one of said first subset of nucleotide analogs comprises said reporter moiety and a first linker moiety.

16. The method of claim 15, wherein said first linker moiety is subjected to a first stimulus, wherein said first linker moiety is cleaved after being subjected to said first stimulus.

17. The method of claim 12, wherein during incorporation, said given one of said first subset of nucleotide analogs and said given one of said second subset of nucleotide analogs are indistinguishable by an enzyme facilitating said incorporation, wherein said enzyme is used to incorporate both said first subset of nucleotide analogs and said second subset of nucleotide analogs.

18. The method of claim 17, wherein said first subset of nucleotide analogs and said second set of nucleotide analogs are structured such that a first Michaelis constant ($K_m$) of a polymerase reaction with said first subset of nucleotide analogs and a second $K_m$ for a polymerase reaction with said second subset of nucleotide analogs are within 30% of one another.

19. The method of claim 17, wherein said first subset of nucleotide analogs and said second subset of nucleotide analogs are structured such that a first maximal rate of reaction ($V_{max}$) of a polymerase reaction with said first subset of nucleotide analogs and a second $V_{max}$ for a polymerase reaction with said second subset of nucleotide analogs are within 30% of one another.

20. The method of claim 12, wherein said given one of said second subset of nucleotide analogs comprises a second linker moiety.

21. The method of claim 20, wherein said second linker moiety is subjected to a second stimulus, wherein said second linker moiety is cleaved after being subjected to said second stimulus.

22. The method of claim 12, wherein said first subset of nucleotide analogs or said second subset of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

23. The method of claim 12, wherein said nucleotide mixture further comprises a third subset of nucleotides or nucleotide analogs, wherein none of said third subset of nucleotides or nucleotide analogs comprises a reporter moiety.

24. A method for analyzing a target nucleic acid molecule, comprising (i) bringing said target nucleic acid molecule immobilized to a support in contact with a nucleotide mixture comprising a first set of nucleotide analogs and a second set of nucleotide analogs, wherein a nucleotide analog of said first set of nucleotide analogs and nucleotide analogs of said second set of nucleotide analogs are different nucleotide analogs but of a same canonical base type, and wherein said first set of nucleotide analogs comprises a reporter moiety detectable by a detector, wherein said second set of nucleotide analogs comprises an analog of said reporter moiety, and wherein said analog of said reporter moiety of said second set of nucleotide analogs does not yield a signal that is detectable by said detector, and (ii) detecting one or more signals from said target nucleic acid molecule, thereby determining at least a portion of a nucleic acid sequence of said target nucleic acid molecule.

25. The method of claim 24, wherein a sum of said first set of nucleotide analogs and said second set of nucleotide analogs is at least 80% of said nucleotide mixture.

26. The method of claim 24, wherein said nucleotide mixture further comprises naturally occurring nucleotides.

27. The method of claim 24, wherein a first given nucleotide analog of said first set of nucleotide analogs comprises a first reporter moiety and wherein a second given nucleotide analog of said second set of nucleotide analogs comprises a second reporter moiety different from said first reporter moiety.

28. The method of claim 24, wherein said one or more signals are detected only from said nucleotide analogs of said first set of nucleotide analogs.

29. The method of claim 24, wherein during incorporation of said nucleotide analogs of said first set of nucleotide analogs and said nucleotide analogs of said second set of nucleotide analogs to said target nucleic acid molecule, a first given nucleotide analog of said first set of nucleotide analogs and a second given nucleotide analog of said second set of nucleotide analogs are indistinguishable by an enzyme facilitating said incorporation, wherein said enzyme is used to incorporate both said first set of nucleotide analogs and said second set of nucleotide analogs.

30. The method of claim 24, wherein said first set of nucleotide analogs or said second set of nucleotide analogs are deoxyuridine-, dideoxyuridine-, deoxyguanosine-, dideoxyguanosine-, deoxyadenosine-, dideoxyadenosine-, deoxythymidine-, dideoxythymidine-, deoxycytidine-, or dideoxycytidine-based nucleotide analogs.

31. The method of claim 24, wherein said nucleotide mixture further comprises a third set of nucleotides or nucleotide analogs, wherein none of said third set of nucleotides or nucleotide analogs comprises a reporter moiety.

32. The method of claim 24, further comprising introducing an additive prior to (ii), wherein said additive prevents misincorporation or changes incorporation rates.

* * * * *

```
                        SEQUENCE LISTING

<160> NUMBER OF SEQ ID NOS: 15

<210> SEQ ID NO 1
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
tcccccccc                                                               10

<210> SEQ ID NO 2
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gggggggga                                                               10

<210> SEQ ID NO 3
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
acggtttctc caacctgtca cctcc                                             25

<210> SEQ ID NO 4
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 4
aaaaaaagga ggtgacaggt tggagaaacc gt                                  32

<210> SEQ ID NO 5
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5 gggggggga ggtgacaggt tggagaaacc gt                                   32

<210> SEQ ID NO 6
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6 ccccccccgga ggtgacaggt tggagaaacc gt                                 32

<210> SEQ ID NO 7
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7 ttttttttgga ggtgacaggt ttttcctgtc acctcc                             36

<210> SEQ ID NO 8
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
acggtttctc caacctgtca cctccuuuuu uu                                  32

<210> SEQ ID NO 9
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
acggtttctc caacctgtca cctccccccc cc                                  32

<210> SEQ ID NO 10
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10 acgtttctc caacctgtca cctccggggg gg                32

<210> SEQ ID NO 11
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
tttttttgga ggtgacaggt ttttcctgtc acctccaaaa aaa        43

<210> SEQ ID NO 12
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
ttgcttgctt gcttgcactg agtcggagac acgcagggat gagatgg    47

<210> SEQ ID NO 13
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
ccatctcatc cctgcgtgtc tccgactcag                30

<210> SEQ ID NO 14
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
tttttgagga ggtgacaggt ttttcctgtc acctcc         36

<210> SEQ ID NO 15
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 15
ggggggggag gtgacaggtt ggagaaaccg t                              31
```